(12) United States Patent
Eskandari et al.

(10) Patent No.: US 8,394,026 B2
(45) Date of Patent: Mar. 12, 2013

(54) METHOD AND APPARATUS FOR DETERMINING VISCOELASTIC PARAMETERS IN TISSUE

(75) Inventors: Hani Eskandari, Vancouver (CA); Septimiu E. Salcudean, Vancouver (CA); Robert N. Rohling, Vancouver (CA)

(73) Assignee: University of British Columbia, Vancouver, British Columbia (CA)

( * ) Notice: Subject to any disclaimer, the term of this patent is extended or adjusted under 35 U.S.C. 154(b) by 620 days.

(21) Appl. No.: 12/611,736

(22) Filed: Nov. 3, 2009

(65) Prior Publication Data
US 2010/0160778 A1 Jun. 24, 2010

Related U.S. Application Data

(60) Provisional application No. 61/193,185, filed on Nov. 3, 2008.

(51) Int. Cl.
*A61B 8/00* (2006.01)
(52) U.S. Cl. ..................................................... 600/438
(58) Field of Classification Search .................. 600/410, 600/437, 438; 382/128
See application file for complete search history.

(56) References Cited

U.S. PATENT DOCUMENTS
2005/0119568 A1 6/2005 Salcudean et al.

OTHER PUBLICATIONS

Walter Maurel; 3D Modeling of the Human Upper Limb Including the Biomechanics of Joints, Muscles and Soft Tissues; Theses No. 1906 (1998) Presentee au department d'informatique; Ecole Polytechnique Federale de Lausanne, EPFL 1999.
Salavat R. Aglyamov et al.; Ultrasound Imaging of Soft Tissue Shear Viscosity; 2003 IEEE Ultrasonics Symposium; pp. 937-940.
Shiya Miyazaki et al.; A Deformable Fast Computation Elastic Model Based on Element Reduction and Reconstruction; Proceedings of the 2004 International Conference on Cyberworlds (CW'04).
Ralph Sinkus et al.; Viscoelastic Shear Properties of in Vivo Breast Lesions Measured by MR Estography; Available online at www.sciencedirect.com; Magnetic Resonance Imaging 23 (2005); pp. 159-165.
A.M. Maniatty et al.; Finite Element Approach to Inverse Problems in Dynamic Elastography; Proceedings of the 5th International Conference on Inverse Problems in Engineering: Theory and Practice, Cambridge, UK, Jul. 11-15, 2005.
Mark L. Palmeri et al.; A Finite-Element Method Model of Soft Tissue Response to Impulsive Acoustic Radiation Force; IEEE Transactions on Ultrasonics, Ferroelectrics, and Frequency Control, vol. 52, No. 10, Oct. 2005; pp. 1699-1712.

(Continued)

*Primary Examiner* — Parikha Mehta
(74) *Attorney, Agent, or Firm* — Lowe Graham Jones PLLC

(57) ABSTRACT

Described herein are a method and apparatus for determining viscoelastic parameters of a tissue. A vibration signal is applied to the tissue and displacements at a plurality of locations within the tissue are measured at a plurality of times. The viscoelastic parameters of the tissue, including elasticity and viscosity, can then be determined by fitting a finite element model of the tissue to the vibration signal and the measured displacements and by solving for the viscoelastic parameters of the model. A value for density of each element of the model is selected and the absolute values for the viscoelastic parameters of each of the elements in the model is determined. Alternatively, the difference in relaxation-times between two locations within the tissue can be determined from the difference in phases of the strains at the two locations.

8 Claims, 15 Drawing Sheets

OTHER PUBLICATIONS

Matthew O.T. Cole et al.; On LMI-Based Optimization of Vibration and Stability in Rotor System Design; American Society of Mechanical Engineers, New York, NY ETATS-UNIS (1984); http://cat.inist.fr/?aModele=afficheN&cpsidt=17915413; Journal of engineering for gas turbines and power, 2006, vol. 128, pp. 672-684.

Ahmad S. Khalil et al.; A Combined FEM/Genetic Algorithm for Vascular Soft Tissue Elasticity Estimation; Published online: Sep. 12, 2006; Springer Science+Business Media, Inc. 2006; pp. 95-104.

M Sridhar et al.; Viscoelasticity Imaging Using Ultrasound: Parameters and Error Analysis; Physics in Medicine and Biology; Published Apr. 10, 2007 online at stacks.iop.org/PMB152/2425; pp. 2425-2443.

Emre Turgay et al., Identifying the Mechanical Properties of Tissue by Ultrasound Strain Imaging, Ultrasound in Med. & Biol., vol. 32, No. 2, pp. 221-235, 2006.

D Fu et al., Non-invasive Quantitative Reconstruction of Tissue Elasticity Using an Iterative Forward Approach, Phys. Med. Biol. 45 (2000) 1495-1509, Printed in the UK, IOP Publishing Ltd.

METHOD AND APPARATUS FOR DETERMINING VISCOELASTIC PARAMETERS IN TISSUE

CROSS REFERENCE TO RELATED APPLICATION

This application claims priority under 35 U.S.C. §119(e) to a U.S. provisional application Ser. No. 61/193,185, filed Nov. 3, 2008, the entirety of which is herein incorporated by reference.

TECHNICAL FIELD

The present invention relates to a method and apparatus for determining one or more viscoelastic parameters in tissue.

BACKGROUND

Viscoelastic parameters of tissue include the elasticity and viscosity of the tissue. These viscoelastic parameters can vary between healthy and diseased regions of tissue. For example, cancerous breast tumors are approximately eight times stiffer than benign lesions while benign lesions are approximately four times stiffer than normal breast tissue (J. Ophir, I. Cespedes, B. Garra, H. Ponnekanti, Y. Huang and N. Maklad, "Elastography: ultrasonic imaging of tissue strain and elastic modulus in vivo," *European Journal of Ultrasound*, vol. 3, no. 1, pp. 49-70, January 1996). Therefore, a doctor examining a patient for a tumor will typically press down on various regions of the patient's body, searching for relatively stiff (highly elastic) regions that could signify the pathology.

Viscosity is also an important mechanical property when assessing tissue health. For example, cancerous lesions with a high blood vessel concentration have a higher viscosity than surrounding, healthy tissue (R. Sinkus, M. Tanter, T. Xydeas, S. Catheline, J. Bercoff, and M. Fink, "Viscoelastic shear properties of in vivo breast lesions measured by MR elastography," *Magnetic Resonance Imaging*, vol. 23, no. 2, pp. 159-165, 2005).

Tissue can be modeled as being composed of a series of interconnected elements, with each element being composed of a mass (m) coupled to a parallel arrangement of a spring having a spring coefficient (k) and a damper having a damping coefficient (b). The spring is used to model the elasticity of the tissue, which is reflected in the tissue's resilience to an applied external force. The damper is used to model the viscosity of the tissue, which is reflected in the tissue's internal friction and relaxation effects. The mass is used to model the density of the tissue. When relatively small applied forces are applied and relatively small displacements result, the force-velocity relationship of the dampers is linear, as is the force-displacement relationship of the springs. All objects with mass exhibit a linear relationship between force and acceleration. One, two or three dimensional arrays of elements are also possible. For an example of a two dimensional array, see FIG. 10 of U.S. Pat. No. 7,731,661 to Salcudean et al., the entirety of which is herein incorporated by reference.

To estimate relative values for elasticity and viscosity in tissue, vibrations can be applied to the tissue and the resulting tissue displacement observed. This can be done over a one, two or three dimensional region and using a variety of imaging modalities; ultrasound and magnetic resonance imaging (MRI) are both modalities that have been used. See, for example, U.S. Ser. No. 10/963,795 to Salcudean et al., and Emre Turgay, Septimu Salcudean, and Robert Rohling, "Identifying the mechanical properties of tissue by ultrasound strain imaging," *Ultrasound in Med. & Biol.*, vol. 32, no. 2, pp. 221-235, 2006, the entirety of which is herein incorporated by reference. By "relative value", it is meant a value for elasticity or viscosity at a certain location within the tissue that is expressed relative to another location within the tissue. A "relative value" is in contrast to an "absolute value", which is a value for elasticity or viscosity that is expressed independently from any other location within the tissue. For example, an absolute value for viscosity is 10 Pas, whereas a relative value for viscosity is 10·x Pas, where "x" is a baseline value for viscosity measured elsewhere in the tissue.

However, prior art methods are often slow and cannot image a tissue region in real-time, can require expensive machinery, or can only determine relative values of viscoelastic parameters.

Consequently, there exists a need for a method and system that addresses one or more deficiencies in the prior art.

BRIEF DESCRIPTION OF THE DRAWINGS

In the accompanying drawings, which illustrate one or more exemplary embodiments.

DETAILED DESCRIPTION

Typical viscoelastic parameters of a region under study that are measured or desirable include elasticity (E), viscosity ($\eta$), and relaxation-time ($\tau$), which is defined as $\tau=\eta/E$. For the purposes of the embodiments discussed herein, the region under study is human tissue, such as breast tissue. The embodiments described herein are directed at a method and apparatus for determining one or more of elasticity, viscosity and relaxation-time. Two approaches are employed to accomplish this.

Figure 1:
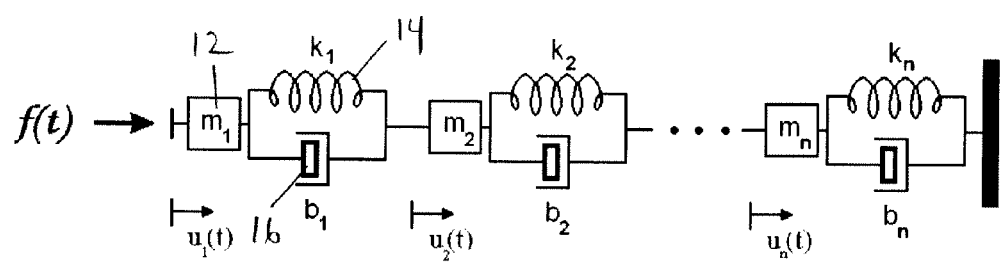
FIG. 1 depicts a one-dimensional mass-spring-damper model of tissue.

Referring now to FIG. 1, the tissue can be modeled as interconnected elements each having a mass (m) 12 coupled to a parallel arrangement of a spring 14 having a spring coefficient (k) and a damper 16 having a damping coefficient (b). The first approach involves assuming that vibration of the tissue is sufficiently slow to be able to ignore the inertial effect of the mass 12, thereby allowing the mass 12 to be removed from the model. Removing the mass 12 from the model allows the tissue region to be modelled as a series of interconnected spring-damper elements. Ignoring the mass 12 of each element is reasonable for a vibration signal of low frequency (e.g.: less than 50 Hz). A "vibration signal" is any externally applied stimulus to tissue that causes tissue deformation that can be measured by means of an imaging modality, such as ultrasound. Due to the vibration signal, tissue is deformed as a function of time.

The tissue model is depicted in FIG. 1. In FIG. 1, the vibration signal is applied to the tissue, which results in an external force f(t) being applied to the tissue. The tissue is divided into elements, with each element extending between two nodes. From the measured axial displacements at the two nodes surrounding any particular element, the strain experienced by that element can be calculated. Following calculation of strain at any two elements, the transfer function relating the strains experienced by those two elements can be calculated. For example, the transfer function $H_2^1(\omega)$ relates the strains between elements 1 and 2 such that $\epsilon_1(\omega) = H_2^1(\omega) \cdot \epsilon_2(\omega)$. In addition to relating strains between any two elements, a transfer function can also be calculated that relates a strain experienced by one element to a stress experienced by a second element, or between a displacement experienced by a first element to a displacement experienced by a second element. This first approach is hereinafter referred to as the "Transfer Function Approach".

The second approach involves assuming that tissue deformation can be modeled by a linear viscoelastic finite element model. Instead of ignoring the mass as is done in the Transfer Function Approach, the density is presumed to be close to 1,000 kg/m$^3$, which is the density of water, since water is the main constituent of most soft tissues. If more accurate and local a priori information of the density in different parts within the tissue are available (e.g.: from textbooks), that information can be incorporated into the model as well. Such a model can be linear or non-linear in the remaining unknown parameters. The linear equations can be solved iteratively or non-iteratively; the equations that are not linear can be solved iteratively. This second approach is hereinafter referred to as the "Finite Element Model Approach" or "FEM Approach".

Both the Transfer Function Approach and the FEM Approach are implemented using the same hardware.

Figure 2:
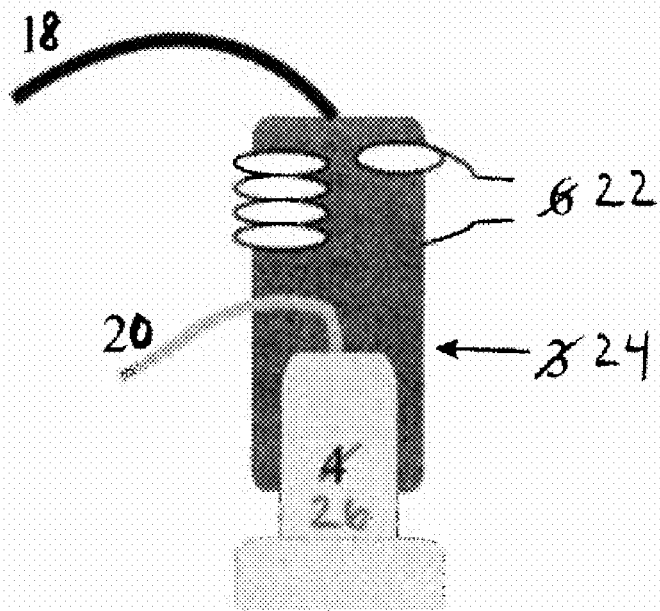
FIG. 2 depicts an ultrasound probe applying a vibration signal to the tissue.

FIG. 2 depicts a handheld actuator 24 that is used to apply a vibration signal to tissue 28. An operator holds the actuator 24 in his or her hand 22. The actuator 24 is connected to an ultrasound imaging system (not shown in FIG. 2) through a cable 18 which drives a motor inside the actuator 24 and which produces motion and, consequently, the vibration signal. The vibration signal can be a filtered wide-band signal covering multiple frequencies (i.e.: be composed of multiple, superimposed frequency components). Alternatively, the vibration signal can be a sinusoidal waveform composed of only a single frequency component. The moving part of the actuator 24 is connected to an ultrasound probe 26 which is in direct contact with or otherwise coupled to the tissue 28, such as by a water-based gel and produces mechanical waves in the tissue 28. The boundary conditions 30 of the tissue 28 may be known, unknown or partially known. While the vibration signal is applied to the tissue 28 via the ultrasound probe 26, the ultrasound probe 26 receives radio-frequency (RF) signals and transmits the signals to the ultrasound machine through a cable 20 for processing and display.

Figure 4:
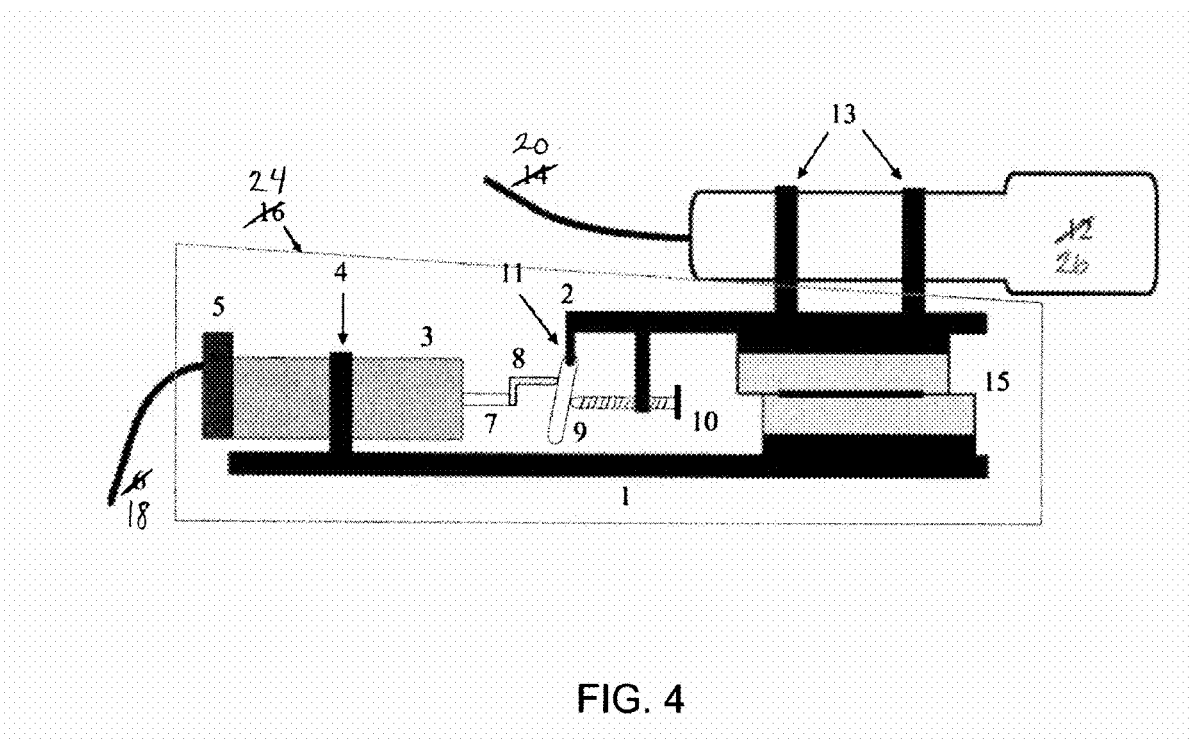
FIG. 4 is a schematic view of a hand-held actuator having the ultrasound probe affixed thereto.

The actuator 24 is shown in more detail in FIG. 4 and can be attached to the ultrasound probe 26 to produce a mechanical stimulus in the tissue. A fastener 13 tightens the ultrasound probe 26 to a vibrating stage 2. The ultrasound probe 26 is connected to the ultrasound machine by the cable 20. A static stage 1 is held by the operator and is connected to the motor 3 by another fastener 4. The motor 3 is connected to an oblique extension 8 by a motor shaft 7. An actuation system transforms motor rotational motion into reciprocating translational motion through a variable angle swash plate 9, in an arrangement similar to that of a swash plate pump. The swash plate angle can be adjusted manually with a screw 10 while the mechanical stimulus is applied. The swash plate 9 is connected to the vibrating stage 2 by a hinge 11. A linear guide 15 ensures linear motion of the vibrating stage 2 with respect to the static stage 1.

Figure 5:
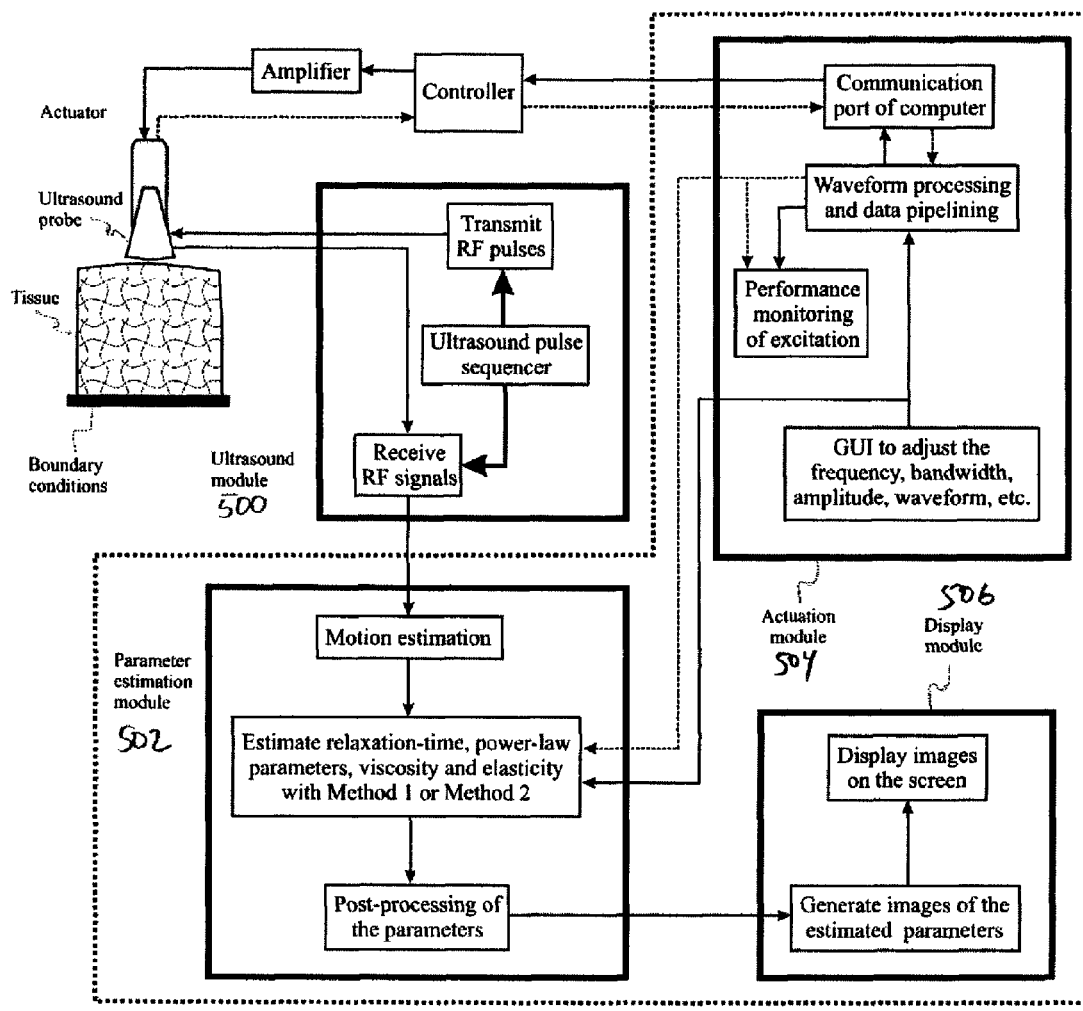
FIG. 5 is a block diagram of a system for determining viscoelastic parameters in tissue, according to one embodiment.

A block diagram of an apparatus for determining viscoelastic parameters in tissue is depicted in FIG. 5. The handheld actuator 24 and ultrasound probe 26 are integrated into a larger system of hardware configured to receive ultrasound data from the tissue 28, determine viscoelastic parameters from the ultrasound data, and the display the viscoelastic parameters to the operator. The probe 26 is pressed over the tissue 28, which is limited by physical boundaries defining the boundary conditions. Included in the system of FIG. 5 is an ultrasound module 500, which is part of the ultrasound imaging system, that transmits ultrasound signals to and receives ultrasound data from the ultrasound probe 26 and controls the ultrasound pulse formation. The ultrasound module 500 transmits data to a parameter estimation module 502 that performs processing steps including, but not limited to, motion estimation, the estimation of relaxation-time and power-law parameters as used in the Transfer Function Approach, the estimation of viscosity and elasticity using finite element modeling as used in the FEM Approach, and post-processing of parameters such as viscosity and elasticity. Post-processing of parameters can include feature extraction and classification of datasets. The transformed data generated in the parameter estimation module is transmitted to a display module 506, which generates image maps of the desired estimated parameters and represents these on a display, which can include a computer monitor. An actuation module 504 drives the mechanical excitation in the hand-held actuator 24. The actuation module 504 transmits a mechanical excitation signal through a controller and an amplifier to drive the actuator 24. The actuation module 504 performs tasks including, but not limited to, waveform processing and data pipelining of the mechanical excitation signal, performance monitoring of the mechanical excitation, and a graphical user interface (GUI) that allows the user to adjust parameters including, but not limited to, the frequency (for the case of a single frequency excitation), bandwidth or frequency range (for a the case of excitation at multiple frequencies), amplitude and waveform shape of the mechanical excitation signal. The parameter estimation module 502, the ultrasound module 500, the actuation module 504 and the display module 506 can form different modules running on hardware such as the ultrasound machine, a general purpose computer, or any suitable data processor coupled to a memory having stored thereon one or more of the modules 500, 502, 504 and 506. Alternatively, any one or more of the modules 500, 502, 504 and 506 can be stored on a computer readable medium such as random access memory and any form of disk based media. Also depicted in FIG. 5 are an amplifier and controller communicatively coupled to the actuator 24, which are part of a driver circuit that drives the actuator 24 to generate the vibration signal.

Figure 3:
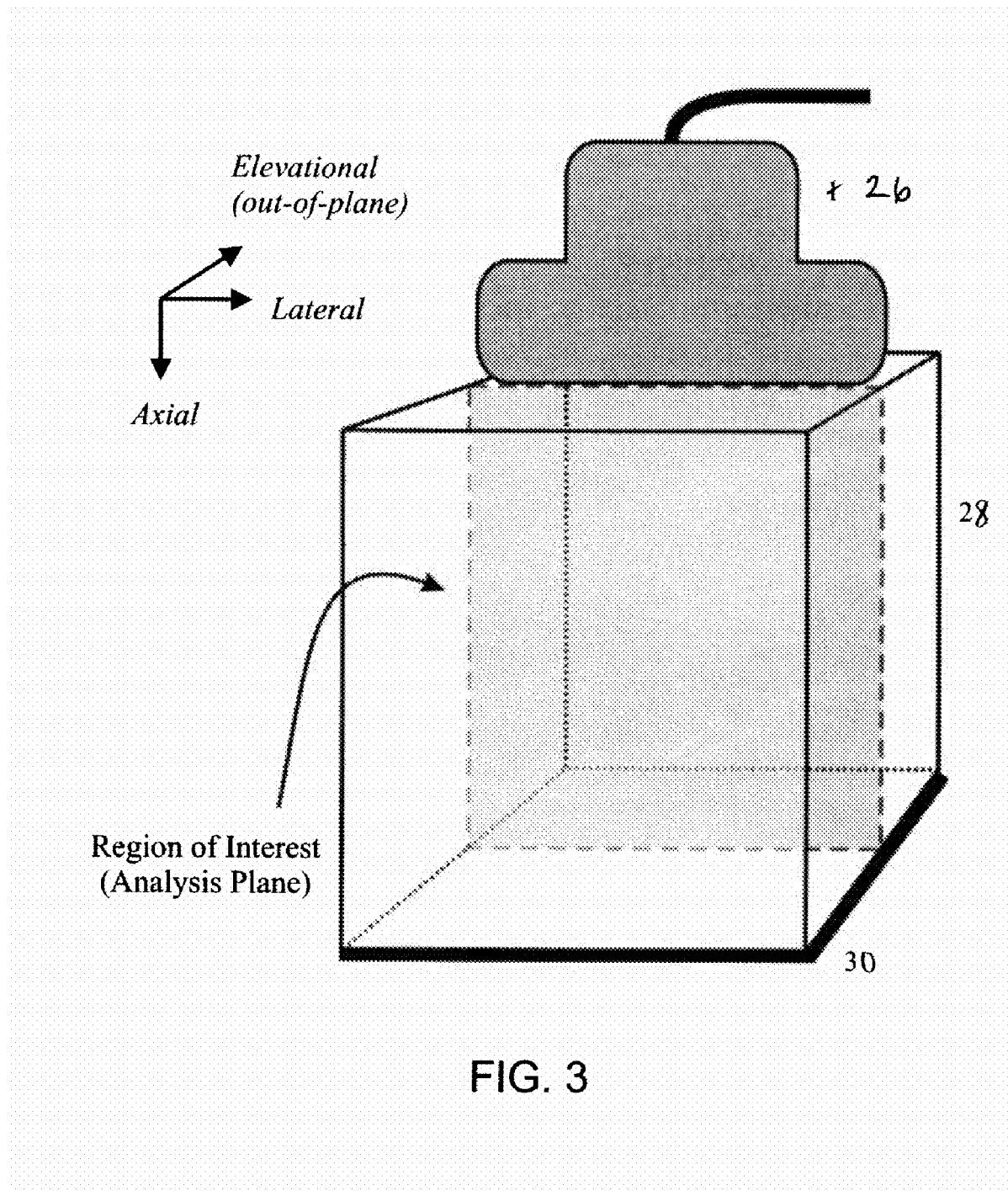
FIG. 3 depicts the ultrasound probe applying the vibration signal to the tissue and illustrates the axial, lateral, and elevational planes of the tissue.

If ultrasound is used as the imaging modality for viscoelasticity measurement of the tissue 28, the ultrasound probe 26 is placed on the surface of the tissue 28 and acquires radio-frequency (RF) data along several A-lines (straight lines extending from the surface of the probe 26) in one, two or three dimensions (1D, 2D or 3D). Therefore, each point in the tissue will have a displacement in 3D which can be projected into axial (along an A-line), lateral (perpendicular to axial in the imaging plane) and elevational (perpendicular to the imaging plane) directions; these directions are depicted in FIG. 3. Axial, lateral and elevational strains are the spatial derivative of such displacements. By applying a Fourier transform or a similar frequency transform to the time-domain displacement or strains, the displacement or strain phasors can be calculated at a desired frequency ($\omega$). For example, the phasor of the axial displacement of a certain location at frequency $\omega$ can be obtained by calculating the Fourier transform of that displacement signal at $\omega$.

Figure 6:
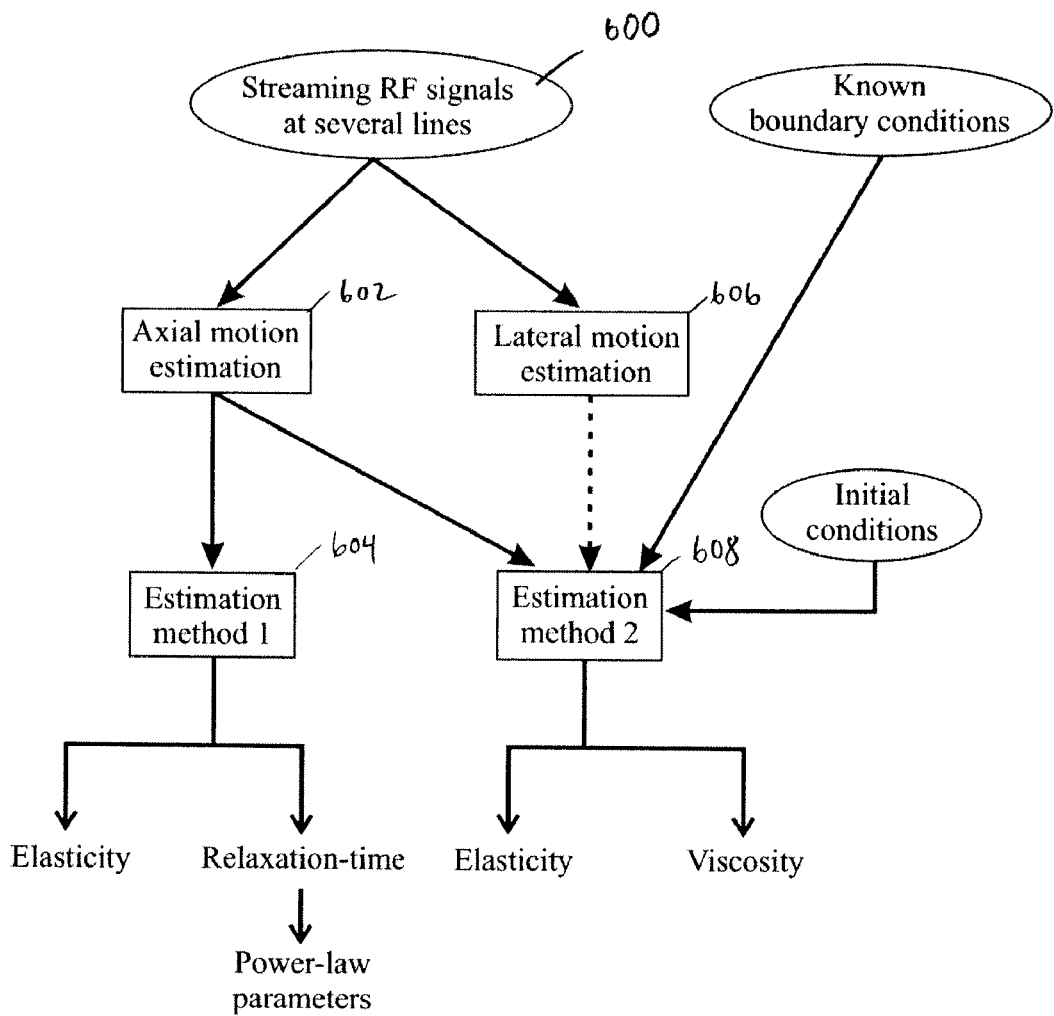
FIG. 6 is a flowchart describing how viscoelastic parameters in the form of elasticity, relaxation-time, and viscosity can be determined.

Referring now to FIG. 6, there is depicted a flowchart describing how viscoelastic parameters in the form of elasticity, relaxation-time, and viscosity can be determined according to the Transfer Function Approach (referred to as "Estimation method 1" in FIG. 6) and a 2D version of the FEM Approach (referred to as "Estimation method 2" in FIG. 6). At block 600, ultrasound RF signals are acquired from the tissue 28. If the Transfer Function Approach is to be employed, axial motion along one dimension of the tissue 28 is derived from the ultrasound RF signals at block 602 and the Transfer Function Approach is employed at block 604, resulting in elasticity and relaxation-time. If a 2D version of the FEM Approach is to be employed, one or both of axial motion and lateral motion is derived from the ultrasound RF signals at blocks 602 and 606, and the FEM Approach is employed at block 608, resulting in absolute values of elasticity and viscosity for each of the elements of the finite element model. Notably, a 3D version of the FEM Approach can also be used, in which axial, lateral and elevational motion are considered.

The Transfer Function Approach and the FEM Approach are now described in turn.

The Transfer Function Approach

When mass 12 is assumed to be zero, the tissue 28 can be modeled as a plurality of elements connected in series, with each element composed of a parallel arrangement of a spring and a damper; this is called a Voigt model, with each element being called a Voigt element. The relationship between stress ($\sigma$) and strain ($\epsilon$) of a Voigt element is $\sigma(t)=E\epsilon(t)+\eta\dot{\epsilon}(t)$, where the dot is the time derivative operator, E is Young's modulus (also known as elasticity), and $\eta$ is the viscosity. In the frequency domain, stress and strain are related by $\hat{\sigma}=(E+j\omega\eta)\hat{\epsilon}$, where the hat operator represents a frequency transform, or phasor. Therefore, by defining relaxation-time as $\tau=\eta/E$, the phase difference between the stress and strain is $\angle\hat{\sigma}-\phi\hat{\epsilon}=\tan^{-1}(\omega\tau)$.

Given that relaxation-time is on the order of milliseconds, at relatively low frequencies (e.g.: less than 50 Hz for typical soft tissues), the phase difference can be approximated as $\angle\hat{\sigma}-\angle\hat{\epsilon}=\omega\tau$. While strain can be measured at all the Voigt elements throughout the tissue, stress values cannot be measured at Voigt elements at interior points of the tissue. Furthermore, accurate measurement of forces at the area of contact between the ultrasound probe 26 and the surface of the tissue requires 2D arrays of force sensors, which may not be practical. However, by assuming a one dimensional spring-damper tissue model, the stress in the tissue can be assumed to be equal everywhere along any given one dimensional line. Consequently, $\omega\tau_1=\omega\tau_0+(\angle\hat{\epsilon}_0-\angle\hat{\epsilon}_1)$ where terms having an index of 0 correspond to a first location on the line and terms having an index of 1 correspond to a second location on the line. The difference in relaxation-times between two locations on the line can therefore be determined from the difference of the phase of the strains between those two locations.

Figure 7:
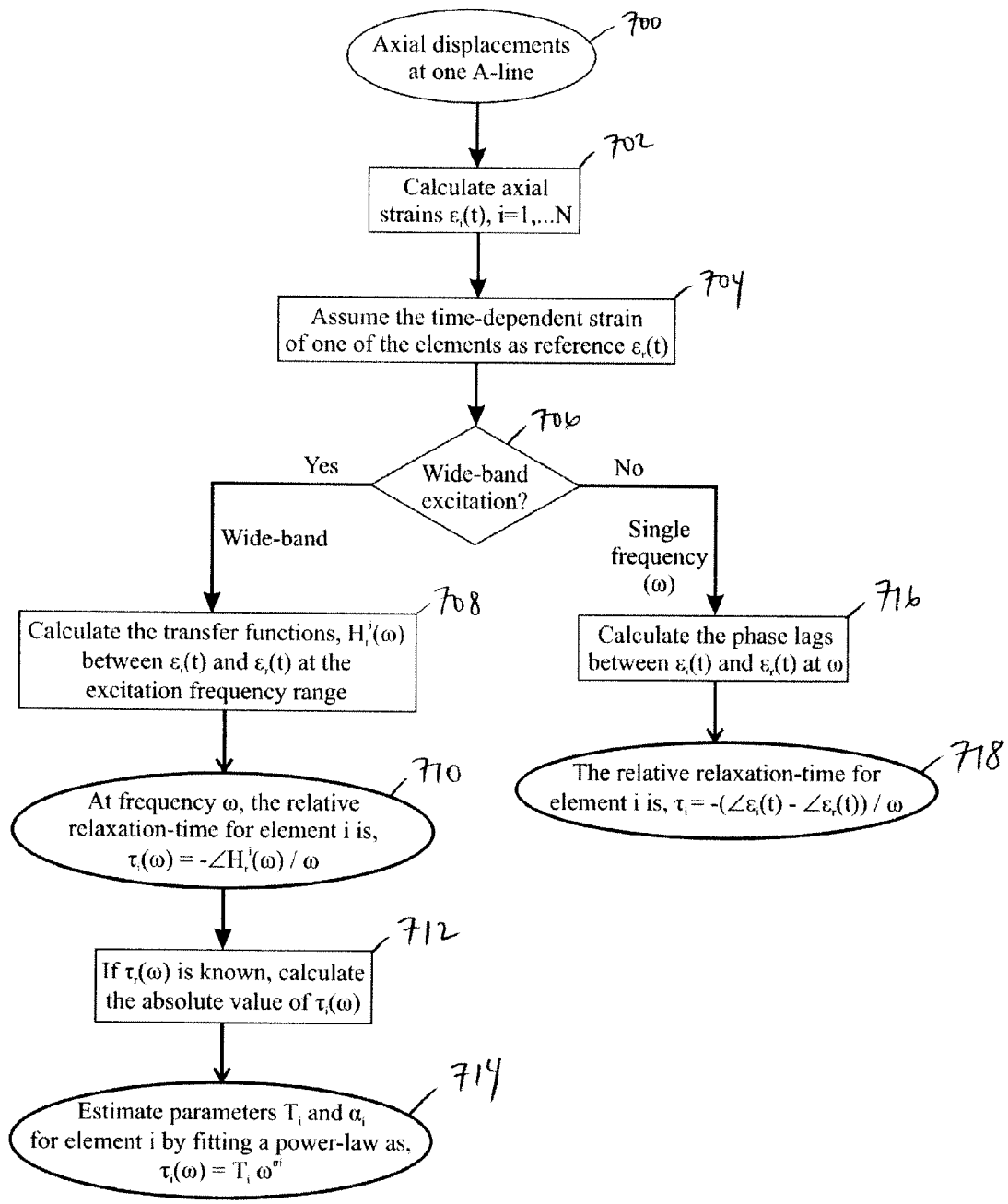
FIG. 7 is a flowchart describing how relaxation-times can be determined according to another embodiment.

Referring now to FIG. 7, there is depicted a flow chart illustrating how relaxation-times of the tissue are calculated in a region of tissue modeled using N Voigt elements. At block 700, axial displacements along one A-line that are caused by application of the vibration force are measured. From the measured axial displacements, the axial strain is calculated at the various elements at block 702. At block 704, the time-dependent strain of one of the Voigt elements ($\epsilon_r$) is used as a baseline value to obtain relative relaxation-time measurements. If the vibration signal includes only a single frequency component (block 706), then at block 716 the phase difference between the strains at the reference element $\epsilon_r$ and the strain at any other element $\epsilon_i$ can be calculated as $\angle\hat{\epsilon}_r-\angle\hat{\epsilon}_i$. From this, the relative relaxation-time of $\epsilon_i$ relative to $\epsilon_r$ is $\tau_i=-(\angle\hat{\epsilon}_i-\angle\hat{\epsilon}_r)/\omega$, as calculated in block 718.

If the vibration signal applied to the tissue 28 is composed of a single frequency component, the phasors can be calculated at that frequency. If the vibration signal has multiple frequency components, the phasors can be calculated at all of the plurality of frequencies. The axial displacement or axial strain phasors can be used with a 1D model of tissue in order to measure the relaxation-time. Transfer functions between the displacement or strain signals at two locations can be calculated at a desired frequency by computing the ratio between their Fourier transforms at that frequency. By "transfer function", it is meant any transformation that yields the ratio of the phasors at the two locations; a transfer function can be determined by calculating the Fourier transform of the two signals and dividing them at a desired frequency. Alternatively, a transfer function can be determined by dividing the cross-spectral density of the two signals by the auto-spectral density of the reference signal.

The transfer functions can be calculated at a single frequency to be able to measure the relaxation-time at that frequency. Alternatively, the transfer functions can be calculated at a plurality of frequencies to measure the relaxation-time at each of those frequencies or averaged to obtain an average of the relaxation-times at those frequencies. If the vibration signal includes multiple, superimposed frequency components, then instead of proceeding to block 716 from block 706, transfer functions $H_r^i(\omega)$ are calculated at block 708. $H_r^i(\omega)$ is the transfer function between strains measured between elements r and i such that $\omega_i(\omega)=H_r^i(\omega)\cdot\epsilon_r(\omega)$. Consequently, the difference in relaxation-time between elements i and r is $$\tau_i(\omega) - \tau_r(\omega) = \frac{-1}{\omega} \angle H_r^i(\omega),$$

as executed at block 710. If the relaxation-time at element r is known, the absolute relaxation-time of element i can be calculated at block 712. In an alternative embodiment (not depicted) in which the stresses ($\sigma$) at elements i and r are known and can be assumed equal, the absolute relaxation-time at any given element, having a strain $\epsilon$, can be calculated as $$\tau = \frac{-1}{\omega} \angle H_\sigma^\varepsilon(\omega),$$

where $H_\sigma^\varepsilon(\omega)$ is the transfer function between the stress and the strain signals.

Figure 8:
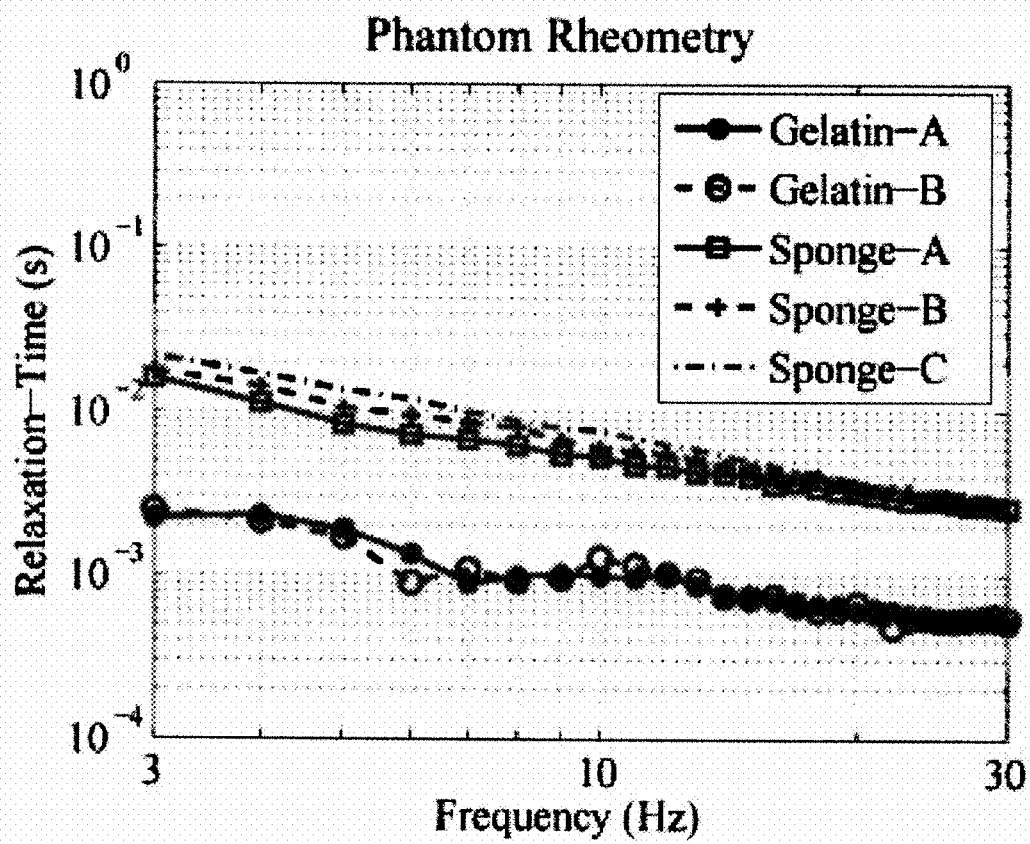
FIG. 8 is a graph of relaxation-time for the tissue vs. frequency, determined according to the embodiment of FIG. 7.

If the relaxation-time is known at one location along a line undergoing dynamic displacement in a specimen through independent calibration or rheometry tests, the relaxation-time can be determined at all frequencies for all the other points on that line. Once such profiles are obtained for the relaxation-times, given the non-Newtonian behavior of soft tissues, a power-law model can be fit to the relaxation-time curves. At block 714, power law parameters (T and α) of every element in the tissue are calculated. The power-law model is used to interpolate the mechanical characteristics of the material at a desired frequency or to use the power-law model parameters for further analysis, feature extraction or classification. Non-Newtonian fluids are those fluids for which the viscosity changes with frequency. Generally, in fluids and soft, viscoelastic solids, the viscosity decreases by a power-law as the frequency increases. FIG. 8 shows the power-law decrease of the relaxation-time for a few tissue mimicking materials, including a soft bovine-skin gelatin phantom (12 wt. % in water)—Gelatin A; a hard gelatin phantom (18 wt. % in water)—Gelatin B; and a wet PVA sponge at three states: completely soaked in water—Sponge C; Partially squeezed—Sponge B; and severely squeezed—Sponge A. The slope of relaxation-time vs. frequency is an additional mechanical characteristic of a viscoelastic material that physicians can use to further characterize different types of tissue.

In alternative embodiments (not depicted), other viscoelastic parameters can be derived from the transfer function $H_r^i(\omega)$ or $H_\sigma^\varepsilon(\omega)$. Above, transfer function phase is used to measure relaxation-time; additionally, Young's modulus can also be obtained from reciprocal of the magnitude of the transfer function between the strain and the stress ($|H_\sigma^\varepsilon(\omega)|^{-1}$), or relative estimation can be obtained from the reciprocal of the magnitude of the transfer function between the two strains at two locations ($|H_r^i(\omega)|^{-1}$). In one embodiment, the viscosity can be estimated by multiplying an estimate of Young's modulus and the relaxation-time at every pixel location. In other embodiments, a power-law model can be fitted to the viscosity as a function of frequency, with the goal of using the frequency-dependency of the viscosity estimate as another power-law parameter for tissue differentiation.

In all of the aforedescribed embodiments, the relaxation-time parameter (τ) or the power-law parameters (T and α) of every block in the tissue can be displayed on the screen to form an image, where the pixel values of the image represent viscoelastic parameters and are calculated in real-time or offline. Physicians can use these images to identify normal and diseased tissues or different types of tissue.

In various embodiments, displacements are used to determine transfer functions. In other embodiments, measurements of strain or displacements in other directions may be used, such as the lateral and elevational directions. For example, the transfer functions can be computed between two different axial displacements, two different lateral displacements, two different lateral strains or between any two points of other components of the displacements or strains.

Parameters derived from the phase of the transfer function, such as relaxation-time and viscosity, can be displayed as an image where pixel values represent the value of the parameter. In some embodiments, an image representing the viscoelastic parameters can be superimposed on a second image such as a conventional ultrasound, MRI, or CT image, to provide context for interpreting the viscoelastic parameters.

The FEM Approach

Introducing mass or density into finite element model (FEM) formulations of viscoelastic materials enables the estimation of the absolute values of the elasticity and viscosity parameters rather than the relative values only even when stress or force is unknown. Such quantitative measurement can be achieved even without having any measurement of the applied force. An FEM model that takes into account the viscous and inertial effects is a discrete representation of the wave equation in a viscoelastic medium. Therefore, quantitative measurement of the viscoelastic parameters can be performed based on knowledge or assumptions about the density of the elements. If the density of all of the elements in the model are known based on a priori knowledge such as from a textbook, that knowledge can be used in the model to estimate the absolute value of the viscoelastic parameters. In most cases, this density distribution is not known exactly, but it is reasonable to assume that water density dominates in soft tissue. Thus the density can be assumed to be 1000 kg/m$^3$. Furthermore, in the absence of force measurements, quantitative measurement of other parameters such as wave speed, kinematic viscosity and relaxation-time can be achieved. With accurate and quantitative characterization of viscosity at different frequencies in this manner, a power-law trend can also be deciphered from the viscosity and/or relaxation-time at different frequencies and the power-law parameters can be estimated and used to identify different tissue types.

Figure 11:
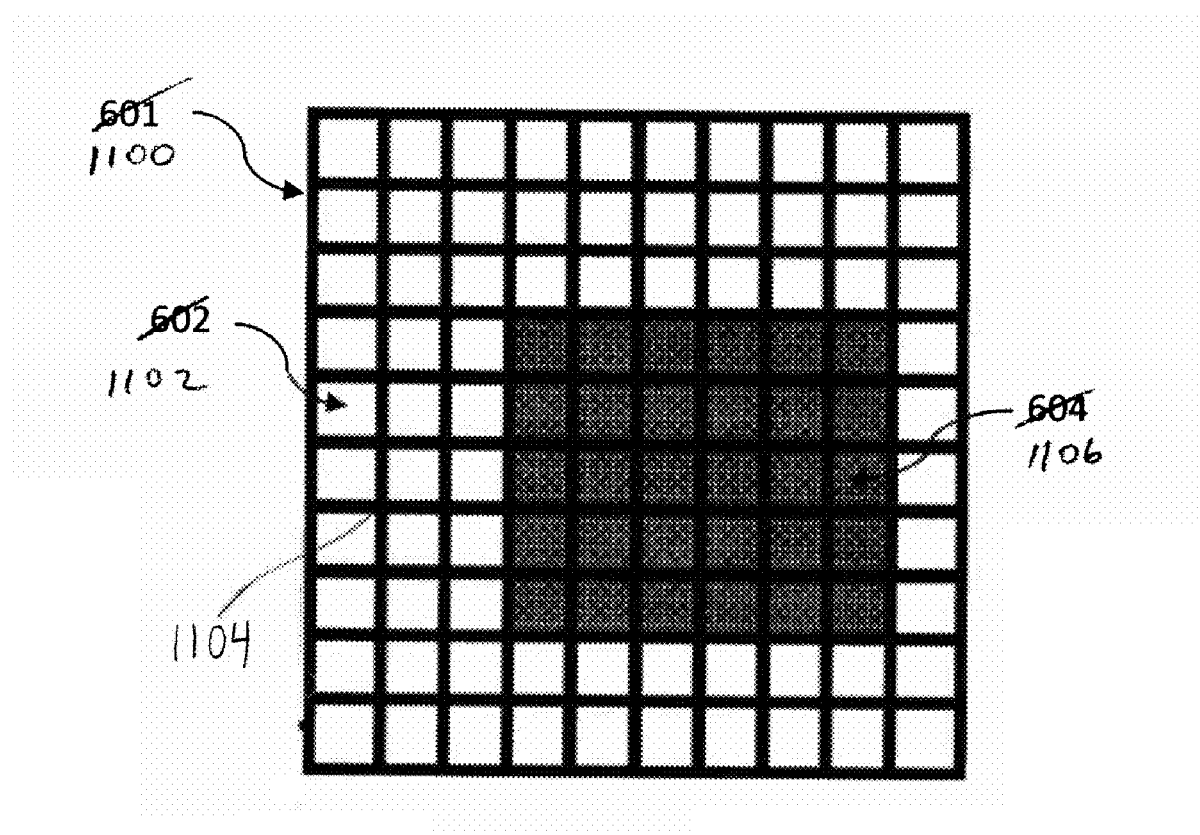
FIG. 11 depicts a two-dimensional region of tissue divided into various segments.

In order to measure the elasticity and viscosity parameters by fitting the measured displacement data to a finite element model, time-domain displacements are measured in 1D, 2D or 3D from a region of interest in tissue. The displacement phasors are calculated from the time domain displacement measurements. The region of interest is meshed by several interconnected elements. Adjacent elements are connected to each other at their vertices, called nodes. The displacements and forces may only be measured on or applied to the nodes of the mesh. FIG. 11 depicts a 2D finite element model mesh 1100 having elements 1102 and nodes 1104.

Each element has an elasticity, a viscosity and a density property. The density is assumed to be a certain value as described above. The displacement phasors are measured at the nodes 1104. Subsequently, the complex-valued displacement phasors are fitted to a frequency-domain representation of the dynamic finite element model and quantitative viscoelastic parameters of all the elements are measured by solving an inverse problem.

The FEM model can represent a 2D or 3D region. In the 2D case, axial and lateral displacements or a subset thereof are required to solve the FEM inverse problem. In the 3D case, axial, lateral and elevational displacements or a subset thereof are required to solve for the viscoelastic parameters of the model. Unlike the Transfer Function Approach, the FEM Approach accounts for 2D and 3D displacement measurements. Furthermore, in the FEM Approach, the viscoelastic parameters can be measured quantitatively without needing to know the applied forces, whereas absolute measurements are not possible without knowing applied forces or stresses in the Transfer Function Approach.

The axial and lateral displacement phasors or time-domain displacement data can be used with a 2D finite element model to measure viscosity and elasticity in a 2D region of interest in the tissue 28. The axial, lateral and elevational displacement phasors or time-domain displacement data can be used with a 3D finite element model to more accurately measure viscosity and elasticity than in a 2D region of interest. If volumetric measurement of displacements are available, the viscoelastic parameters can be similarly measured for a volume, using a 3D FEM model.

In the FEM Approach, the tissue 28 is divided into elements 1102 for which viscoelastic parameters are derived based on a fit to a model that satisfies input and output signals. The input signals are the nodal boundary conditions and the output signals are the displacements of the interior nodes 1104 of the model. The nodal boundary conditions are the displacements at the boundaries of the tissue 28 or the external forces to the model. These external forces are usually not measured, although it is possible in specific cases to measure the pattern of forces applied by the actuator 24. To represent the viscoelastic characteristics of the tissue 28 the following transient FEM model is used, with the displacement vector u(t) describing the motion at all the nodes 1104 in response to applied external nodal forces f(t):

$$Ku(t)+B\dot{u}(t)+M\ddot{u}(t)=f(t) \quad (1)$$

where K is the stiffness matrix which depends on the elements' elasticity values, concatenated into a vector E; B is the viscous damping matrix which depends on the elements' viscosities, concatenated into a vector η; and M is the mass matrix which depends on the elements' densities, concatenated into a vector p. Assuming lumped masses at the nodes 1104 of the FEM model results in M being a diagonal matrix.

For a linear FEM model, each entry of the K matrix, called the stiffness matrix, is a linear combination of the elasticities of the elements 1102 in the model. Similarly, the entries of B, called the damping matrix, and M, called the mass matrix, are linearly dependent on the element viscosities and densities, respectively. Any technique as is known to a person skilled in the art can be used to construct the K, B and M matrices in an FEM model.

In one embodiment, the damping matrix can be constructed for every element 1102 from the stress-strain relationship in a linear viscoelastic medium. In this embodiment, the damping matrix of every element 1102 is linearly dependent on the viscosity of the tissue 28 at that element 1102. The global damping matrix B is then obtained by combining the individual damping matrices for each element 1102. In this manner, the entries of the damping matrix B will be linearly dependent on the viscosity of the elements 1102.

To derive B according to this embodiment, note that the stress tensor ($\sigma_{ij}$) in the Cartesian coordinate system for a viscoelastic material can be written as follows, $$\sigma_{ij}=\lambda\epsilon_{kk}\delta_{ij}+2\mu\epsilon_{ij}+\lambda'\dot{\epsilon}_{kk}\delta_{ij}+2\mu'\dot{\epsilon}_{ij}, \quad (1a)$$

The strain tensor is denoted by $\epsilon_{ij}$ and its time derivative by $\dot{\epsilon}_{ij}$. Tensor notation is used; thus $\epsilon_{kk}=\epsilon_{11}+\epsilon_{22}+\epsilon_{33}$ and the Kronecker delta $\delta_{ij}=1$ if i=j and 0 if i≠j. The subscript indices correspond to orthogonal directions in the Cartesian coordinate system. λ and μ are the Lamé constants and λ' and μ' are the viscosity characteristic parameters. In most fluids and rubber-like materials, the bulk viscosity which is defined as κ=λ'+2μ'/3 is approximately zero, thus λ'=−2μ'/3. The vector notation of (1a) is:

$$\sigma=C\epsilon+C'\dot{\epsilon}, \quad (1b)$$

where vectors $\sigma=[\sigma_{11}\ \sigma_{22}\ \sigma_{33}\ \sigma_{23}\ \sigma_{31}\ \sigma_{12}]^T$ and $\epsilon=[\epsilon_{11}\ \epsilon_{22}\ \epsilon_{33}\ \epsilon_{23}\ \epsilon_{31}\ \epsilon_{12}]^T$ contain the six components of the isotropic stress and strain tensors in the general 3D setting. In (1b), C is the material elasticity characteristic matrix which can be derived from (1a). C' is the material viscosity characteristic matrix which can be derived from (1a) with the zero bulk viscosity assumption:

$$C' = \frac{2}{3}\mu' \begin{pmatrix} 2 & -1 & -1 & 0 & 0 & 0 \\ -1 & 2 & -1 & 0 & 0 & 0 \\ -1 & -1 & 2 & 0 & 0 & 0 \\ 0 & 0 & 0 & 3 & 0 & 0 \\ 0 & 0 & 0 & 0 & 3 & 0 \\ 0 & 0 & 0 & 0 & 0 & 3 \end{pmatrix}. \quad (1c)$$

While the above notation is for a 3D FEM problem, for a 2D case the matrices C and C' can be reduced by assuming plane-stress or plane-strain as known to the skilled in the art. For each element 1102, the viscous damping matrix B can be produced by integrating (1b) over the entire element with appropriate shape functions.

Given that the entries of K are also linearly dependent on the elasticity of the elements 1102, the FEM equations can be established as a system of equations that are linear in the viscoelastic parameters. Beneficially, when constructing the damping matrix according to this embodiment, a linear system of equations can be obtained which can be solved, as described in greater detail below.

Conventional methods of constructing the damping matrix B do not yield a linear system of equations. For example, in one method of constructing the damping matrix known as the Rayleigh damping, the damping matrix is a linear combination of the stiffness and mass matrices, $B=\xi_1 K+\xi_2 M$, where $\xi_1$ and $\xi_2$ are constant coefficients that describe the dependence of B on K and M. In this representation, the viscosity of the elements are not incorporated into the damping matrix and the FEM system of equations will not be linear in the viscosity parameters of the elements 1102. Therefore, the preferred approach is not to use the standard damping matrix formulation, which leads to a non-linear dependence on parameters, but rather employ the linear stress-strain relationship in a viscoelastic medium to construct the damping matrix.

By taking the Fourier transform of Equation (1), the linear FEM formulation of the tissue in the frequency domain is $$(K+j\omega B-\omega^2 M)\hat{u}=\hat{f} \quad (2)$$

where hatted variables denote Fourier transforms and j is the imaginary unit. Noting that û and f̂ are complex-valued vectors, equation (2) can be decomposed into its real and imaginary components:

$$(K+j\omega B-\omega^2 M)(\hat{u}^r+j\hat{u}^i)=\hat{f}^r+j\hat{f}^i \quad (3)$$

where superscripts r and i represent the real and imaginary components, respectively, and j is the imaginary unit.

By decomposing û and f̂ into their real and imaginary parts, equations (2) and (3) can be written as:

$$A\begin{bmatrix} \hat{u}^r \\ \hat{u}^i \end{bmatrix} = \begin{bmatrix} \hat{f}^r \\ \hat{f}^i \end{bmatrix} \quad (4)$$

where the superscripts r and i denote the real and imaginary components of a vector, respectively. A is defined as follows:

$$A = \begin{bmatrix} K-\omega^2 M & -\omega B \\ \omega B & K-\omega^2 M \end{bmatrix}. \quad (5)$$

If the viscoelastic parameters of the FEM model are known, the problem of solving for the displacement vector u as a result of a known force vector f and certain displacement boundary conditions is called the forward problem. If the displacements are known and Equations (4) and (5) are solved for the elasticity and viscosity of the elements, it is the inverse problem that is solved. Note that the elasticity and viscosity of the elements have linear relationships with the entries of the matrices K and B, respectively.

Two approaches can be employed to solve the inverse problem. In a first approach, Equations (4) and (5) can be solved in an iterative fashion, without assuming linearity in the unknown viscoelastic parameters. In a second approach, the linearity of Equations (4) and (5) in the unknown viscoelastic parameters can be exploited by solving Equations (4) and (5) with either an iterative or non-iterative method. Note that Equation (4) describes a system of equations that is linear in the viscoelastic parameters. In the first approach, the linearity in parameters is not exploited in finding a solution. In the second approach, the linearity in parameters is exploited by using standard methods to solve a linear system of equations.

Solving Equations (3) and (4) Iteratively, without Assuming Linearity

To be able to solve the forward problem to obtain the displacements at the interior nodes 1104, given a distribution of the viscoelastic parameters, the displacement boundary conditions can be incorporated into Equation (2), as is known to persons skilled in the art. This procedure involves changing the externally applied forces on the right hand side of Equation (2), as well as the corresponding rows in the K, B and M matrices on the left-hand side of Equation (2), to account for the displacement at the boundary, instead of the force. This way, a new left-hand side matrix and right hand side vector are obtained, subscripted by c, as in the following equation:

$$G_c \begin{bmatrix} \hat{u}^r \\ \hat{u}^i \end{bmatrix} = \begin{bmatrix} \hat{f}_c^r \\ \hat{f}_c^i \end{bmatrix} \tag{6}$$

The subscript c indicates that the corresponding matrix or vector has been manipulated to replace the equations corresponding to the unknown external forces by the corresponding displacement boundary conditions. $G_c$ is defined as follows:

$$G_c = \begin{bmatrix} K_c - \omega^2 M_c & -\omega B_c \\ \omega B_c & K_c - \omega^2 M_c \end{bmatrix} \tag{7}$$

Without displacement boundary conditions, solving Equation (4) for the tissue elasticity and viscosity in the region of interest is an ill-posed problem. After applying the displacement boundary conditions, Equation (6) is well-posed and can be solved to obtain the displacements in the interior region.

As an example, we assume that there is only one non-zero entry ($f_0$) in the force vector which has to be replaced by the corresponding known displacement boundary condition ($u_0 = U0^r$). Therefore, assuming that the first column of G in (4) is $[g_{11}, g_{21} \ldots g_{ng1}]^T$, where ng is the number of rows in G, Equation (4) will change to:

$$\begin{bmatrix} 1 & 0 & \cdots & 0 \\ 0 & & & \\ \vdots & & G_{s11} & \\ 0 & & & \end{bmatrix} \begin{bmatrix} \hat{u}^r \\ \hat{u}^i \end{bmatrix} = \begin{bmatrix} U0^r \\ -g_{21} U0^r \\ \vdots \\ -g_{ng1} U0^r \end{bmatrix} \tag{7e}$$

where $G_{s11}$ is a matrix of G obtained by removing the first row and the first column of G. The resulting left-hand side matrix is $G_c$ in (6) that is computed for this example and the resulting right-hand side vector is the $$\begin{bmatrix} \hat{f}_c^r \\ \hat{f}_c^i \end{bmatrix}$$

vector that is calculated for this example.

In solving the inverse problem, the optimal values of Young's moduli and viscosities of the elements 1104 are determined iteratively to fit the model according to the observed displacement vectors. To solve the inverse problem iteratively and determine optimal values for Young's modulus and viscosity, a cost function can be used to measure deviation of predicted displacements with estimated parameters from measured displacements. The cost function can be defined according to Equation (8).

$$\Phi(p) = \frac{1}{2}\|\hat{u}^r(p) - \hat{u}_0^r\|^2 + \frac{\alpha}{2}\|\hat{u}^i(p) - \hat{u}_0^i\|^2 \tag{8}$$

In this equation, $p = [E^T \ \eta^T]^T$ is a 2 m parameter vector composed of elasticity and viscosity parameters, considering that there are m elements in the FEM model. The parameter $\alpha$ is a weight determining the relative importance of the imaginary and real components of the displacement in the inverse problem. $\alpha$ can simply be equal to one. The Euclidean norm of a vector is denoted by $\|.\|$.

A number of cost functions similar to (8) can be utilized to solve for model parameters, and the function in (8) has been used only as an example of a particular embodiment.

The parameter vector p can be updated using an iterative procedure including, but not limited to, the modified Gauss-Newton method, the Levenberg-Marquardt algorithm or any other method that finds a set of parameters that minimizes a cost function such as Equation (8). In the present embodiment, the parameter vector is updated iteratively as, $p_{k+1} = p_k + \Delta p_k$, $k = 1, 2, \ldots$, where k is the iteration index. The update vector $\Delta p_k$ is to be calculated from:

$$H_k \Delta p_k = -J_k^T \Delta \hat{u}_k, \tag{9}$$

where $J_k$ is the Jacobian, $H_k$ is the Hessian and $\Delta \hat{u}_k$ is defined as follows:

$$\Delta \hat{u}_k = \begin{bmatrix} \Delta \hat{u}_k^r \\ \Delta \hat{u}_k^i \end{bmatrix} = \begin{bmatrix} \hat{u}_k^r - \hat{u}_0^r \\ \hat{u}_k^i - \hat{u}_0^i \end{bmatrix}, \tag{10}$$

where, for simplicity $\hat{u}_k$ denotes $\hat{u}(p_k)$. By applying the chain rule to calculate the derivative of (6), the following results:

$$\frac{\partial G_c}{\partial p_j}\begin{bmatrix}\hat{u}^r\\ \hat{u}^i\end{bmatrix} + G_c\{J_j\} = \begin{bmatrix}\frac{\partial \hat{f}^r}{\partial p_j}\\ \frac{\partial \hat{f}^i}{\partial p_j}\end{bmatrix}, \quad (11)$$

where $\{J_j\}$ denotes the $j^{th}$ column of the Jacobian matrix. Note that $p_j$ can be either elasticity or viscosity of an element, therefore $\partial G_c/\partial p_j$ can be computed from (7) as follows:

$$\frac{\partial G_c}{\partial p_j} = \begin{cases}\begin{bmatrix}\frac{\partial K}{\partial e_j} & 0\\ 0 & \frac{\partial K}{\partial e_j}\end{bmatrix}, & p_j = e_j\\ \omega\begin{bmatrix}0 & -\frac{\partial B}{\partial \eta_j}\\ \frac{\partial B}{\partial \eta_j} & 0\end{bmatrix}, & p_j = \eta_j\end{cases} \quad (12)$$

Given that $G_c$ is known, Equation (11) can be solved for $\{J_j\}$ and thus the Jacobian matrix can be constructed.

To solve for $\Delta p_k$ in equation (9), the Hessian at iteration k is calculated using (13).

$$H_k = J_k^T J_k + \lambda_k I_{2m \times 2m}, \quad (10)$$

In (10), $I_{2m \times 2m}$ is an identity matrix with m being the number of elements, and $\lambda_k$ is a small regularization factor that makes the $H_k$ positive definite.

In alternative embodiments, a spatial filter can be applied to the elasticity and viscosity distributions at every iteration to make the solution of the problem smooth and less sensitive to the displacement noise. As a result, the elasticity or viscosity parameter of each element 1102 will be a weighted sum of its own value and the values of that parameters in the adjacent elements 1102. A linear filter can thus be constructed in the form of a sparse matrix that contains the required weights for each element 1102. The filter can be convolved with the updated distribution of the parameter at every iteration to conduct the optimization toward a smooth solution.

Figure 9:
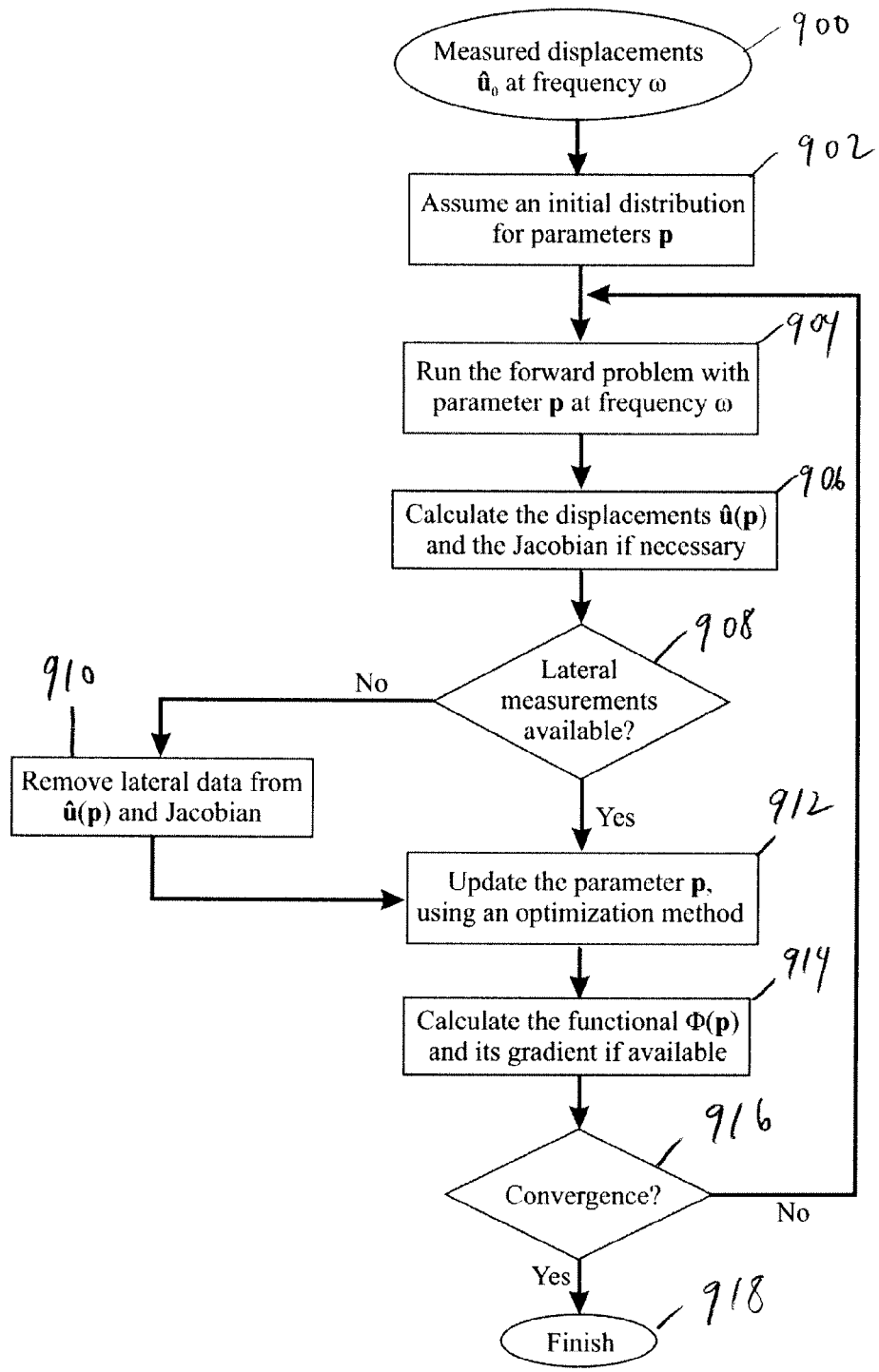
FIG. 9 is a flowchart describing how viscoelastic parameters can be iteratively solved, according to another embodiment.

Referring now to FIG. 9, there is depicted a method for solving Equations (6) and (7) iteratively, which can be executed on an ultrasound machine. Beginning at block 900, a user measures displacements phasors $\hat{u}_0$ at a given frequency $\omega$. At block 902, an initial distribution for p is assumed and, subsequently, at block 904, $\hat{u}(p)$ is determined based on the value of p assumed at block 4902. The initial guess for p can be found by setting all elasticity parameters and all the viscosity parameters of the different elements in the FEM model equal to each other. For example, all the elasticity values can be initialized to 20 kPa and all the viscosity values can be initialized to 20 Pas. At block 908 the processor can check whether lateral displacements were measured in the interior of the region of interest of the tissue 28 or not. If lateral displacements were measured, the processor proceeds to block 912, where p is updated using an optimization method such as that described in Equation (9). However, if the lateral displacements were not measured, the columns of the Jacobian that correspond to those lateral displacements can be removed and a reduced Jacobian can be obtained (block 410). This reduced Jacobian can then be used to calculate the Hessian as described above, and to solve for $\Delta p_k$ in Equation (9) using only the axial portion of $\Delta \hat{u}_k$, and $p$ can be updated in block 912. If lateral displacements are not measured, $\phi(p)$ will be measured based on the differences in the axial displacements only. At block 914, $\phi(p)$ and its gradient are calculated. The value of $\phi(p)$ is an indication of how close to the optimal solution the current parameter value is, while its gradient indicates how slowly or quickly the procedure is converging. Whether or not one of these convergence criteria are met is checked at block 916. If the convergence criterion is not met, the procedure is repeated beginning at block 904. If the convergence criterion is met, then the method finishes at block 918.

Solving Equations (3) and (4) Assuming Linearity in the Parameters, Either Non-Iteratively or Iteratively Deriving Ap=b When assuming linearity, a series of equations are obtained from the finite element model in the form of Ap=b, where p represents the viscoelastic properties, i.e. the elasticities and viscosities of all the elements in the model. The description below provides the specific procedure used in this embodiment to obtain a linear system of equations in the form of Ap=b from the finite element model in Equation (3).

Starting from Equation (3), the entries of the stiffness matrix K, are formed as a linear combination of the elasticity parameters of the elements:

$$K_{l,q} = \sum_{z=1}^{m} c_{l,q}^z E^z, \quad (14)$$

where $c_{l,q}^z$ are constant coefficients that are determined by the type of mesh and geometry. Furthermore, m is the number of elements and $K_{l,q}$ refers to an entry on row l and column q of the stiffness matrix. Similarly, the global damping matrix and global mass matrix are linearly dependent on the viscosity and density parameters, respectively.

Given that the entries of K are linearly dependent on the elasticity of the elements, the entries of vectors $K\hat{u}^r$ and $K\hat{u}^i$ from (3) are also linearly dependent on the elasticity of the elements. For instance, the $l^{th}$ entry of $K\hat{u}^r$, is as follows:

$$[K\hat{u}^r]^l = \sum_{q=1}^{dn} K_{l,q}\hat{u}_q^r, \quad (15)$$

where n is the number of nodes in the model and d is the number of dimensions in the problem which is equal to 2 for 2D and 3 for 3D cases. Substituting the expression for $K_{l,g}$ from (14) into (15) and reformulating that as a vector-vector product:

$$\begin{aligned}[K\hat{u}^r]^l &= \sum_{q=1}^{dn}\sum_{z=1}^{m} c_{l,q}^z E^z \hat{u}_q^r \\ &= C_l^{Er^T} E,\end{aligned} \quad (16)$$

where E is the elasticity vector and $C_l^{Er}$ is a vector defined as follows:

$$C_l^{Er^T} = \sum_{q=1}^{dn} \hat{u}_q^r c_{(l,q)}^T, \quad (17)$$

Given that one element of the vector $K\hat{u}^r$ can be calculated through a vector-vector multiplication, the entire $K\hat{u}^r$ vector can be computed by performing a matrix-vector multiplication as follows:

$$K\hat{u}^r = C^{Er}E, \quad (18)$$

where the superscripts E and r indicate that this coefficient matrix corresponds to the elasticity parameters and was constructed using the real part of the displacement vector. Similarly, for all of the combinations in (3):

$$K\hat{u}^r = C^{Er}E,$$
$$K\hat{u}^i = C^{Ei}E,$$
$$B\hat{u}^r = C^{\eta r}\eta,$$
$$B\hat{u}^i = C^{\eta i}\eta,$$
$$M\hat{u}^r = C^{\rho r}\rho,$$
$$M\hat{u}^i = C^{\rho i}\rho, \quad (19)$$

where $\eta$ and $\rho$ are the vectors containing the viscosities and densities of the elements. By substituting (19) into (3) and splitting the real and imaginary parts into separate equations, the following results:

$$\begin{bmatrix} C^{Er} & -\omega C^{\eta i} \\ C^{Ei} & \omega C^{\eta r} \end{bmatrix} \begin{bmatrix} E \\ \eta \end{bmatrix} = \omega^2 \begin{bmatrix} C^{\rho r} \\ C^{\rho i} \end{bmatrix} \rho + \begin{bmatrix} \hat{f}^r \\ \hat{f}^i \end{bmatrix}. \quad (20)$$

The rightmost term in (20) is the external force vector of the FEM. Note that the entries of the force vector are zero everywhere except for a few nodes 1104 to which the external excitation is applied. The equations that correspond to non-zero forces can be removed from the rows of the matrices in (20). The following model is thus obtained which represents a system of equations that is linear in the parameters p:

$$Ap = b \quad (21)$$

where, $$A = \begin{bmatrix} C^{Er} & -\omega C^{\eta i} \\ C^{Ei} & \omega C^{\eta r} \end{bmatrix}_R, \quad (22)$$

$$p = \begin{bmatrix} E \\ \eta \end{bmatrix}, \quad (23)$$

$$b = \omega^2 \begin{bmatrix} C^{\rho r} \\ C^{\rho i} \end{bmatrix}_R \rho, \quad (24)$$

where the subscript R denotes that the corresponding matrices are reduced in size by eliminating the rows that correspond to the externally applied forces.

As an example, assume that there is only one non-zero entry $(f_0)$ in the force vector which has to be eliminated from the equations. Assuming that $f_0$ is the first entry in the force vector, on the right-hand side of (20), the first rows of the matrices (20) and consequently the first equation in the system of equations described by (20) should be removed. The remaining system of equations can be described as in (21).

Equation (21) can be solved for parameters p, if the unknown external forces are removed from the equations. Therefore, the rows in A and b that correspond to unknown external forces are removed. To calculate A and b based on row elimination for unknown forces, two cases should be considered. In the first case, if a node 1104 has a zero external force component in a specific direction, the corresponding row in the matrices in (20) should not be changed or removed. In the second case, if a node 1104 has a non-zero external force component at a specific direction, the corresponding row should be removed from equation (20) to be able to solve (21).

In solving (21), A is a known matrix which depends on the mesh, region of interest, frequency and measured displacements. The variable p is the unknown parameter vector comprising elasticity and viscosity parameters of all of the elements. The vector b is a known vector which depends on the mesh, region of interest, frequency, measured displacements and density of the elements 1102. As discussed above, the density can be assumed to be a known value, and approximately equal to that of water (1000 kg/m$^3$) for all elements. Alternatively, the density is not assumed to be constant across all elements but is assumed to be known based on a priori knowledge, such as from textbooks on the typical properties of a tissue type.

In an alternative embodiment, the unknown force entries can be inserted into the unknown parameter vector, p, instead of being removed. In this case, one column should be added to the A matrix for each unknown force entry. Therefore the problem can be solved simultaneously for the absolute values of the viscoelastic parameters as well as the unknown forces, assuming that there are more equations than unknowns in the system. For example, assume that there is only one unknown force entry, $f_0$, which is real-valued and applied to the first node. In this case equation (21) holds, while equations (22-24) will be changed to:

$$A = \begin{bmatrix} C^{Er} & -\omega C^{\eta i} & -1 \\ C^{Ei} & \omega C^{\eta r} & 0 \end{bmatrix}, \quad (22e)$$

$$p = \begin{bmatrix} E \\ \eta \\ f_0 \end{bmatrix}, \quad (23e)$$

$$b = \omega^2 \begin{bmatrix} C^{\rho r} \\ C^{\rho i} \end{bmatrix} \rho, \quad (24e)$$

where, −1 in (22e) is a scalar while 0 is a vector of zeros. By using (22e) and (24e) in (21), the absolute values of the viscoelastic parameters and unknown force in (23e) can be measured.

In another embodiment, the finite element equations of the viscoelastic model are analyzed in the time domain (1) to measure the quantitative values of the parameters. In this embodiment, a time sequence of displacements is measured and used in the time-domain representation of the dynamic finite element model. Therefore, an equation similar to (19) can be derived with time-domain displacement matrices instead of real or imaginary displacement phasors. As a result, a similar equation to (20) but with larger matrices can be obtained and the same procedure can be used to solve the resulting system of equations. Absolute values of the elasticity and viscosity parameters of all of the elements can be obtained by solving an inverse problem.

It is possible to solve for p in (21) if there exist more equations compared to the number of unknown parameters. Therefore, after elimination of the unknown external forces, the number of unknown parameters must be less than the number of equations in (21).

Considering a 2D FEM mesh with m×n nodes, comprising rectangular elements, the number of all the available equations is equal to the two times the number of nodes (2mn). The number of unknown viscoelastic parameters for all the elements is two times the number of elements (2(m−1)(n−1)= 2mn−2(m+n−1)). Therefore, there are 2(m+n−1) more equations than unknowns in the case where there is one set of measurements at one frequency. In this case, in order to be able to solve the inverse problem, the number of unknown entries in the force vector cannot be more than 2(m+n−1). A similar calculation can be performed for the 3D FEM model and for different types of elements.

The number of equations in the system of equations can be increased by incorporating more displacement measurements. In one embodiment, more displacement measurements at two or more frequencies increase the number of equations. For example, by having measurements at two frequencies instead of only one frequency, and incorporating them into the A matrix in (21), the number of rows in A will double. As a result, more robust estimates of the parameters can be obtained. Incorporating multiple sets of displacements at multiple frequencies into A is also useful to reduce the sensitivity to the measurement noise in the displacements. Therefore, even if there are sufficient number of equations to solve the problem, displacements at multiple frequencies can be used to construct A and obtain a more robust estimate of the viscoelastic parameters.

If the elimination of the unknown entries from the force vector results in insufficient number of equations to solve for all of the parameters, other element reduction techniques can be performed as described below.

Parameters derived from the finite element model such as viscosity and elasticity can be displayed as an image where pixel values represent the values of the particular parameter of interest. In some embodiments, an image representing the viscoelastic parameters can be superimposed on a second image to give additional information, and to give a context for interpreting the viscoelastic parameters. The second image can be, for example, an ultrasound image, a magnetic resonance image, or a computed tomography image.

Solving Ap=b

Equation (21) can be solved in different ways, as described below.

(a) Solving the Unconstrained Problem

If there are no additional equality or inequality constraints on the variables, Equation (21) can be solved by employing several algorithms to solve a minimum least squares problem. In one embodiment of this approach, $A^T$ can be pre-multiplied by the two sides of (11) to obtain the following solution for p:

$$p = (A^T A)^{-1} A^T b \quad (25)$$

Here, p can be computed using techniques known to persons skilled in the art.

In another embodiment of this approach, (21) can be solved using iterative strategies such as the conjugate gradient method. Alternatively, (21) can be solved using singular value decomposition, Cholesky factorization or QR factorization.

In another approach, instrumental variables can be used to solve (21). In one embodiment of this approach, an instrument matrix $A_v$ can be used to pre-multiply the two sides of (21). This gives:

$$A_v^T A p = A_v^T b \quad (26)$$

Here again, p can be computed as is known to persons skilled in the art.

The instrument matrix should have low or zero correlation with the measurement noise embedded in A. The instrumental variables technique can be applied in a recursive way to improve the estimation of p with time. The instrument matrix is generated in the same way as A, but using a different set of measurements. In one embodiment, the instrument matrices can be computed from the measurements at a different time instance. Alternatively, the instrument matrices can be computed from the measurements at a different frequency.

The instrumental variable technique has been applied in other fields such as process control identification, but has not been used before in the estimation of mechanical or viscoelastic parameters of tissue. Advantageously, it provides for the accumulation of measurements in order to determine more reliable parameter estimates. Without its use, noise in the measurements can cause the estimates to severely underestimate the actual parameter values.

(b) Solving the Constrained Problem

Linear Programming (Non-iterative)

In another approach, a linear programming technique can be used to solve (21). In one embodiment of this approach, a convex optimization problem can be set up in which the minimization functional is zero or any constant scalar. In such a linear programming problem, (21) can be applied as a constraint to the problem. Other linear equality and inequality constraints can be added to the optimization problem while maintaining its "linear program" formulation. For example, the elasticity and viscosity parameters of the model can be constrained within a range that is known for soft tissue. Furthermore, a limit can be imposed on the spatial variation of the parameters. For example, an inequality constraint can be assumed on a linear combination of the parameters Quadratic Programming (Iterative)

Another approach to solve (21) is to set up the problem as a quadratic program and solve it using one of the various methods to solve a quadratic program. The quadratic program can be defined as follows:

$$\min_p \frac{1}{2} p^T H p + z^T p \quad (27)$$

Linear equality and inequality constraints on the parameters of the model, as described above for the case of a linear program, can be added to the optimization problem while maintaining its "quadratic program" formation. In one embodiment of this approach, a cost function can be defined as $\|Ap-b\|^2$, and can be expanded as:

$$\|Ap-b\|^2 = p^T A^T A p - 2b^T A p + b^T b \quad (28)$$

Knowing that $b^T b$ is a scalar and does not affect the minimization, from (21) and (28), it can be deduced that:

$$H = 2A^T A, \quad (29)$$

$$z = -2A^T b, \quad (30)$$

Therefore, the following quadratic program is obtained:

$$\min_p p^T A^T A p - 2 b^T A p, \quad (32)$$

$$\text{subject to } \begin{cases} A_{eq} p = b_{eq} \\ lb \leq A_i p \leq ub, \end{cases}$$

where $A_{eq}$ and $A_i$ are matrices that comprise the coefficients of the equality and inequality constraints, respectively. $b_{eq}$, lb and ub are vectors defining the equality constraints, lower and upper bounds, respectively.

In another embodiment of this approach, the instrumental variable method can be used to set up the minimization problem as a quadratic programming method with or without additional constraints on the parameters.

Elimination of the Parameters in the Finite Element Model Using Equality Constraints A limited number of elements 1102 can be assumed to have the same viscoelastic parameters. This way, the number of unknown parameters in the problem will be reduced and the inverse problem can be solved for the viscoelastic parameters. Assuming that certain elements 1102 have the same parameters is known as imposing "equality constraints".

In one embodiment, a limited number of adjacent elements 1102 can be assumed to have the same viscoelastic parameters. This condition can be applied to the aforementioned constrained optimization methods as a few equality constrains to equate the viscoelastic parameters to those adjacent elements. In this way, the number of unknown parameters in the problem can be reduced and the inverse problem can be solved more easily without significantly affecting the results for parameters removed from these adjacent elements.

In another embodiment of this approach, the tissue 28 is divided into one or more sets of segments, such that the viscoelastic parameters for all of the elements 1102 inside each segment are constant. In FIG. 11, for example, shaded area 1106 represent a segment in which all elements 1102 have the same viscosity and elasticity values. The number of unknown parameters will only be twice the number of segments, as all the elements 1102 in the segment share common elasticity and viscosity parameters. This way, the number of the unknown parameters will be reduced and solving the FEM inverse problem will be more efficient.

Alternatively, this can be implemented by assuming several equality constraints between elements. As an example of this approach, if a tumor is detected or suspected by a clinician, its boundaries can be delineated and a region of interest can be defined to enclose the tumor. The entire region of interest can be divided into two segments with different viscoelastic properties. Thus the absolute elasticity and viscosity can be measured inside the tumor and in the background tissue. In this manner, a characterization of the tumor properties is possible in an efficient way and the processing unit can measure and display the parameters at a faster rate, enabling real-time imaging.

According to another embodiment, homogeneity of the parameters in the entire region can be assumed, thus measuring the absolute values of only two parameters, such as elasticity and viscosity, of the homogeneous region, without knowing the forces.

Figure 10:
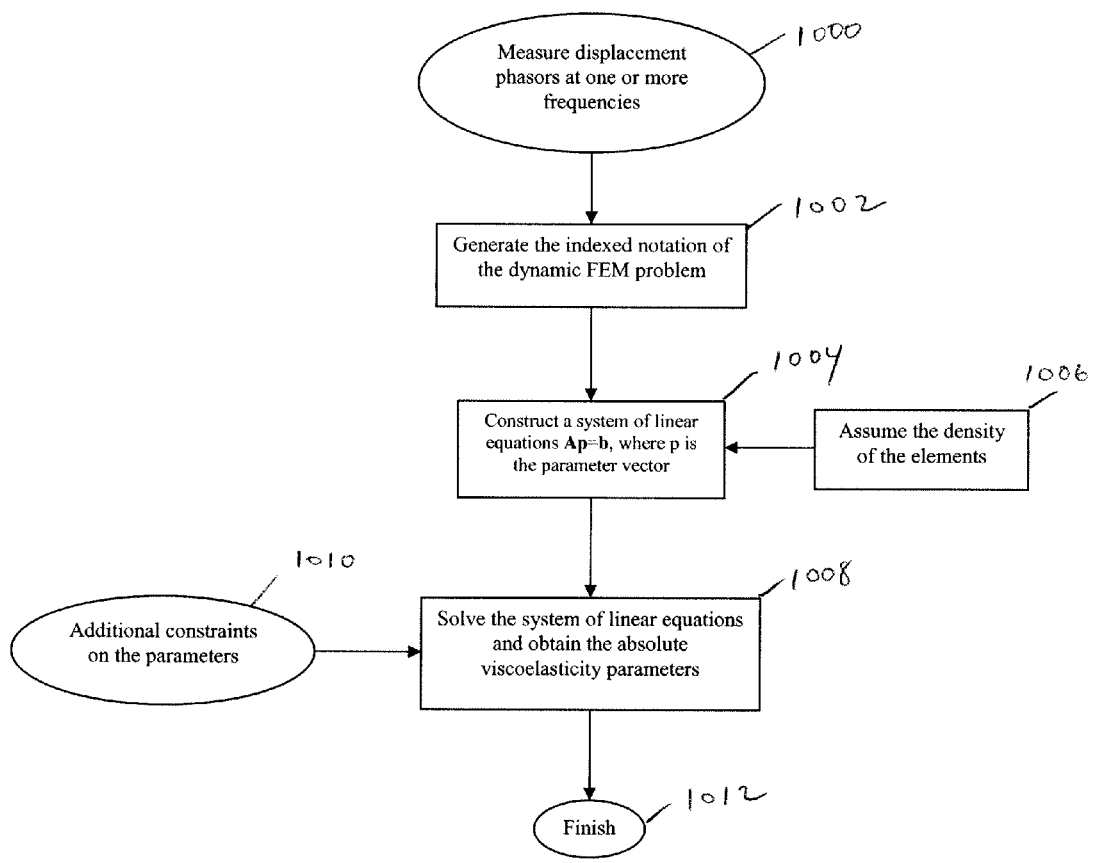
FIG. 10 is a flowchart depicting how viscoelastic parameters can be non-iteratively solved, according to another embodiment.

Referring now to FIG. 10, there is depicted a flowchart explaining how the parameter estimation module 502 can solve the linear system of equations Ap=b. At block 1000, the operator acquires data by measuring displacements within the tissue 28 using the ultrasound probe 26. Following data acquisition, at block 1002 the parameter estimation module 502 generates an indexed notation of the finite element model problem, as described in Equations (20) and (21). Subsequently, at block 1004, the parameter estimation module 502 constructs a system of linear equations in the form Ap=b as described in Equations (21) through (24). The density of the elements of the finite element model is assumed to be a certain value, for example the density of water, at block 1006. The system of linear equations is subsequently solved at block 1008, optionally taking into account any constraints at block 1010. At block 1012, the parameter estimation module 502 has solved the equations.

Application to Other Imaging Modalities

Aside from ultrasound, other imaging modalities, such as magnetic resonance imaging (MRI) and computed tomography (CT), can also be used to acquire axial and lateral displacements of tissue in response to a mechanical excitation.

EXAMPLES

Example 1

Figure 12:
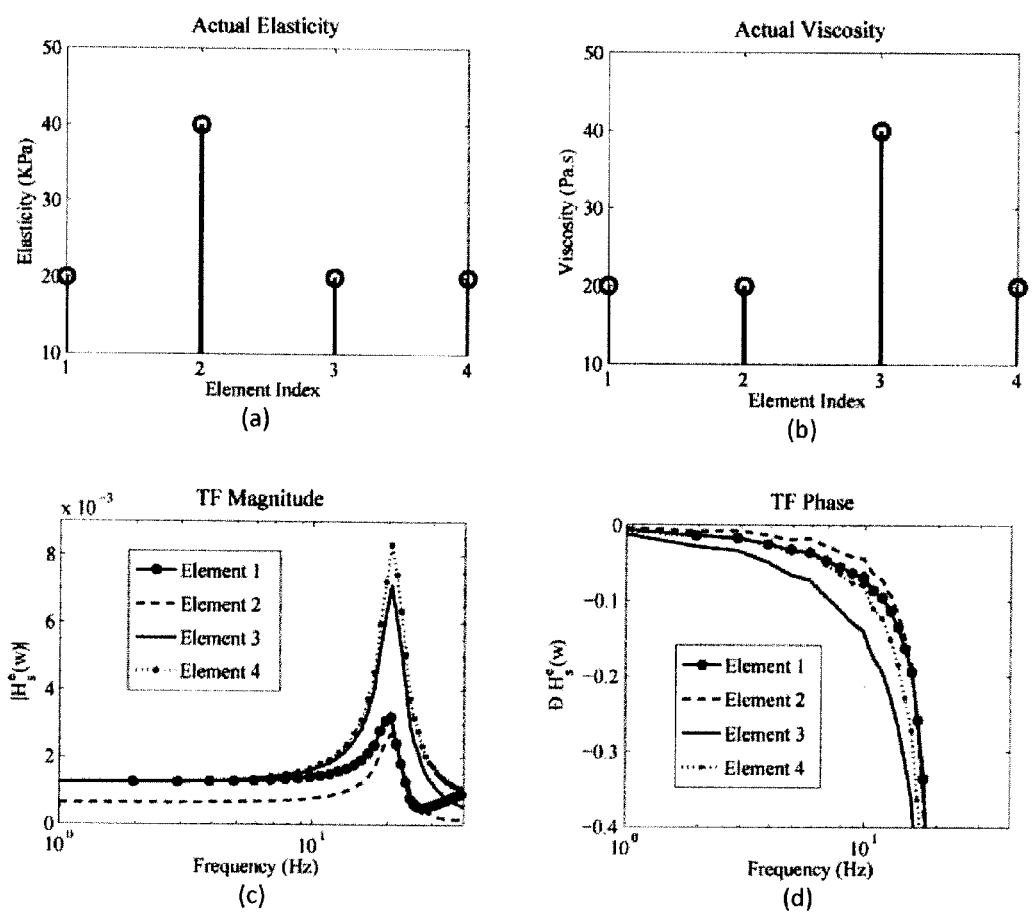
FIG. 12 depicts graphs of transfer functions determined according to the embodiment of FIG. 7.

Using the Transfer Function Approach to Derive Relaxation-Time: Numerical Results A medium with four Voigt elements has been simulated with the elasticity and viscosity as shown in FIGS. 12(a) and 12(b), respectively. A wide-band motion has been applied to the first node and the time-dependent displacements and strains have been calculated. The magnitude and phase of the transfer functions between the stress and strains are shown in FIGS. 12(c) and 12(d). Note that the low-frequency behavior of the magnitude of the spectrum correlates with the elasticity of the medium, while the slope of the phase depends on the local relaxation-times.

Example 2

Using the FEM Approach to Determine Viscoelastic Properties in a PVC Phantom

Figure 13A:
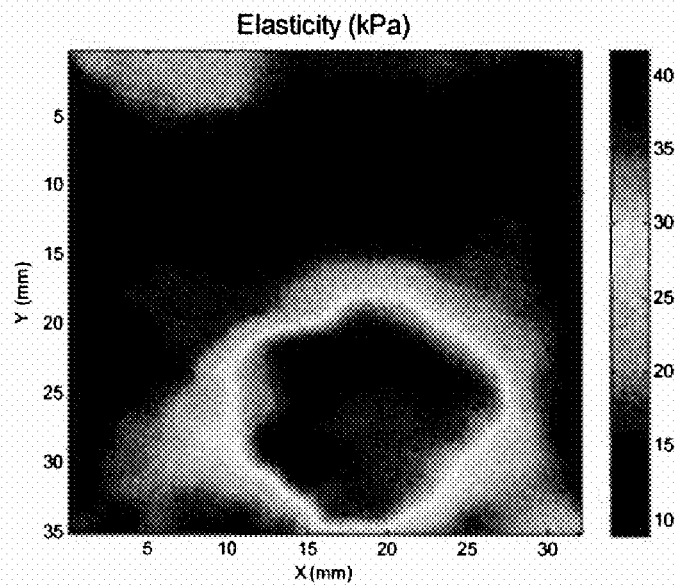
FIGS. 13 through 15(b) depict images of viscosity and elasticity determined in accordance with the aforementioned embodiments.
Figure 13B:
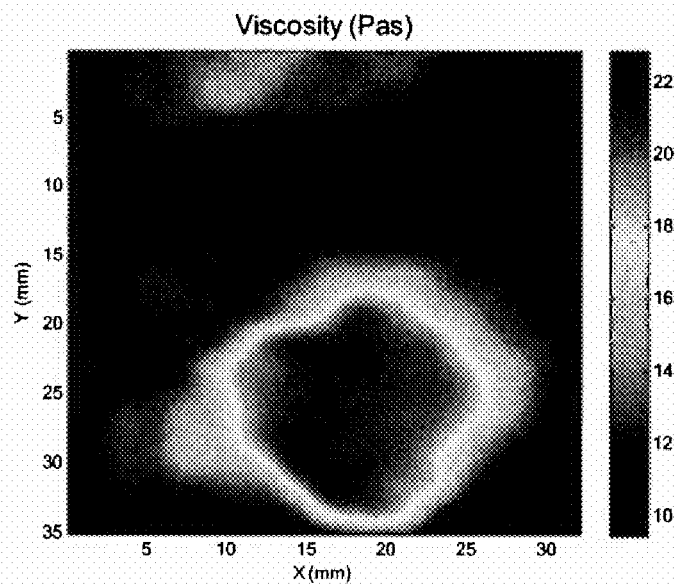

The FEM Approach was used to reconstruct elasticity and viscosity of a cubic PVC phantom (6 cm×5 cm×3 cm) with a hard circular inclusion. The images were produced as follows: an ultrasound linear probe acquired RF data at 98 frames per second from the top of the phantom for approximately 1 second while an actuator was applying 20 Hz vibration to the phantom from below, having a peak-to-peak amplitude of less than 1 mm. Radiofrequency data were collected from a 4 cm×4 cm region in 2D. Two dimensional displacements were calculated and their real and imaginary parts were computed at 20 Hz and the quadratic programming method was used to estimate the absolute values of the elasticity and viscosity using a finite element model. FIGS. 13(a) and 13(b) show the reconstructed elasticity and viscosity maps of the PVC phantom with a hard circular inclusion. The absolute value of the elasticity is close to the palpable elasticity of the phantom.

Example 3

Using the FEM Approach to Determine Viscoelastic Properties in a Gelatin Phantom A tissue mimicking phantom (38 mm×40 mm×25 mm) has been constructed with 12% (by weight) bovine skin gelatin in water. A small piece of a polyvinyl alcohol (PVA) sponge was embedded in the phantom. Based on independent rheometric measurements, the background gelatin had a Young's modulus and a viscosity of approximately 15 kPa and 15 Pas respectively at 10.7 Hz. The sponge was approximately three times harder and 15 times more viscous than the background at that frequency.

The phantom was placed on an actuator and ultrasound RF data were captured using a linear probe positioned at the top of the phantom. A wide-band displacement excitation (1-30 Hz) with a Gaussian amplitude distribution with standard deviation of 44 μm was applied to the bottom of the phantom. The internal motion of the phantom was estimated using a cross-correlation based algorithm. Frequency analysis was performed on the displacements and the real and imaginary parts at 10.7 Hz were selected to solve the inverse problem by minimizing a convex functional iteratively. The estimated contrast of the elasticity and viscosity between the background and inclusion are in agreement with the rheometric measurements of the viscoelastic properties as noted above.

Figure 14A:
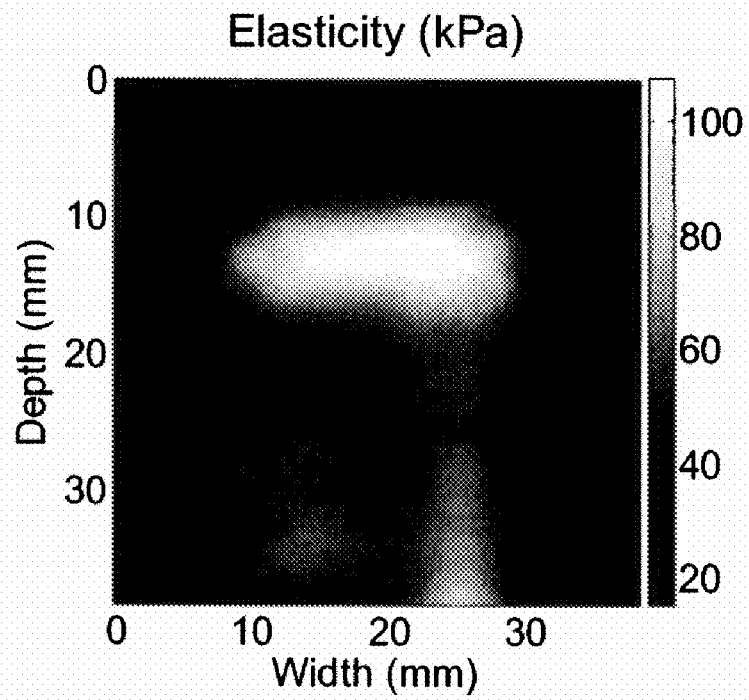
Figure 14B:
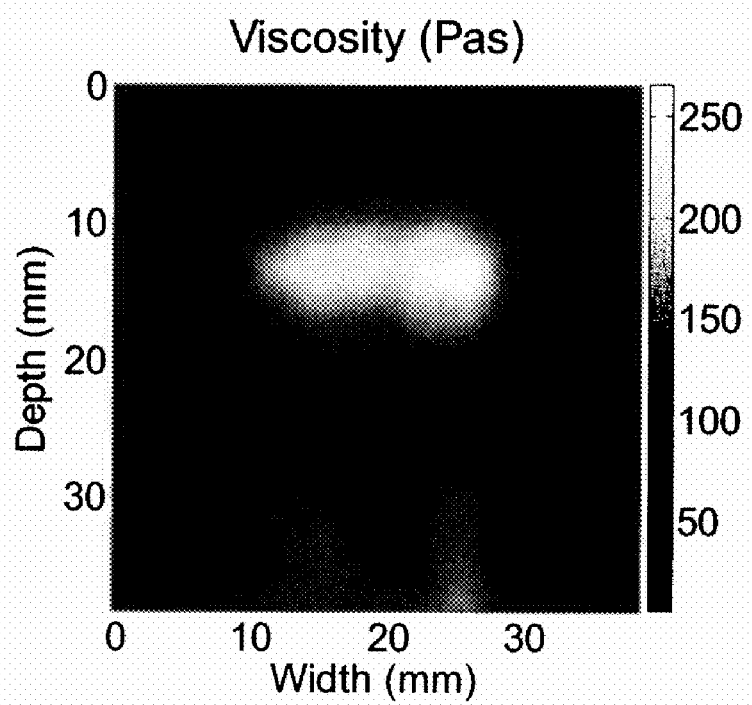

The elasticity and viscosity distributions measured in the phantom are depicted in FIGS. 14(*a*) and 14(*b*), respectively.

Example 4

Using the Transfer Function Approach to Determine Relaxation-Time in a Phantom

Figure 15A:
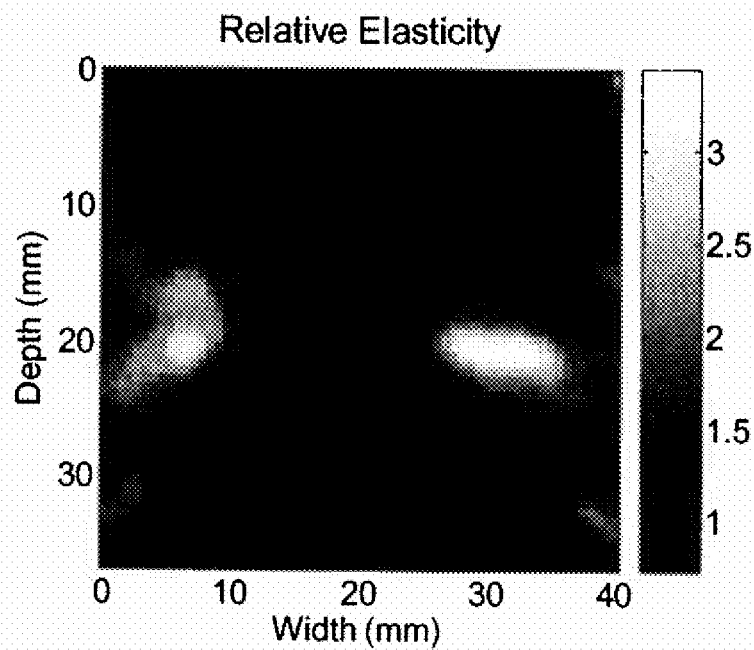
Figure 15B:
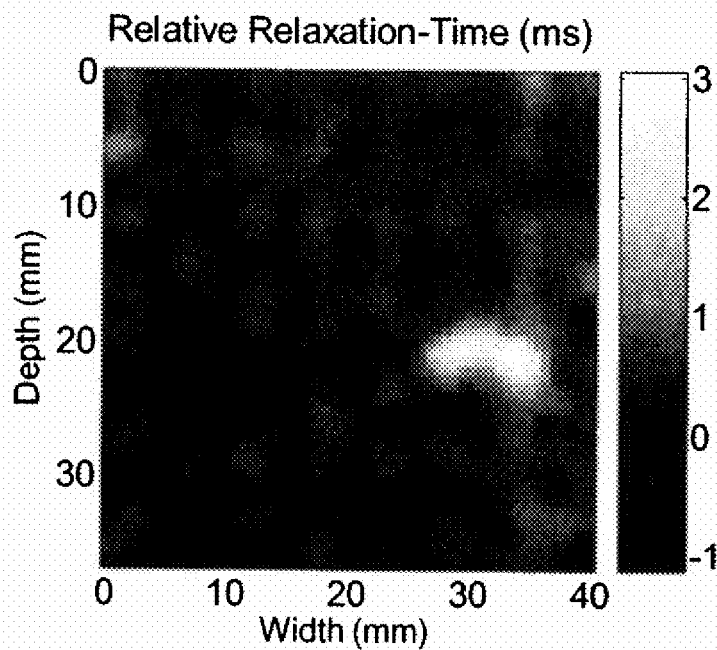

A DC motor was used to apply a wideband excitation (3-30 Hz) to the phantom from the bottom, with less than 0.3% overall strain. RF data was acquired at 98 frames per second over a 40 mm imaging window from the top of the phantom. The phantom was constructed from 12% bovine skin gelatin. A hard gelatin inclusion (18% by weight) was placed on the left side of the phantom while a small PVA sponge inclusion was embedded on the other side of the phantom. Axial displacements were calculated and the transfer functions between the strains at every line were computed. The asymptotic magnitude of the transfer function between 3 Hz and 10 Hz was used to generate the relative elasticity image and the phase of the transfer functions at 15 Hz was used to generate the relative relaxation-time image of the phantom. The relative values between the backgrounds and inclusion are in agreement with independent rheometric measurements. The relative elasticity and relaxation-time images are depicted in FIGS. 15(*a*) and 15(*b*), respectively. The images indicate that while both inclusions are harder than the background material, only the sponge inclusion has a significantly higher relaxation-time compared to the surrounding gelatin.

While particular embodiments have been described in the foregoing, it is to be understood that other embodiments are possible and are intended to be included herein. It will be clear to any person skilled in the art that modifications of and adjustments to the above embodiments, not shown, are possible.

The invention claimed is:

1. A method for determining viscoelastic parameters of a tissue, the method comprising:
    (a) applying a vibration signal to the tissue;
    (b) measuring displacements at a plurality of locations within the tissue in response to the vibration signal at a plurality of times and calculating strains at two locations within the tissue;
    (c) estimating a difference in relaxation-times between the two locations from a difference in phases of the strains at the two locations.

2. A method as claimed in claim 1 wherein estimating the difference in relaxation-times at a frequency comprises dividing the difference in phases of the strains at the two locations by the frequency.

3. A method as claimed in claim 1 wherein estimating the difference in relaxation-times comprises determining a transfer function relating the strain between the two locations and estimating the difference in relaxation-times therefrom.

4. A method as claimed in claim 1 further comprising:
    (a) determining additional relaxation-times at different frequencies at the two locations; and
    (b) fitting a power-law model to a relaxation-time curve comprising the additional relaxation-times plotted against the different frequencies.

5. A method as claimed in claim 3 wherein estimating the difference in relaxation-times at a frequency comprises dividing a difference in phase of the transfer function between the two locations by the frequency.

6. A method as claimed in claim 3 wherein the transfer function is a first order transfer function.

7. A method as claimed in claim 5 further comprising determining an absolute value of the relaxation-time at one of the two locations from an absolute value of the relaxation-time at the other of the two locations.

8. An apparatus for determining viscoelastic parameters of a tissue, the apparatus comprising:
    (a) an actuator for generating a vibration signal and applying a generated vibration signal to the tissue;
    (b) a driver circuit communicatively coupled to the actuator and configured to drive the actuator to generate a vibration signal having at least one frequency component;
    (c) an ultrasound imaging system configured to determine tissue displacement at a plurality of locations within the tissue in response to the vibration signal at a plurality of times; and
    (d) a data processor communicatively coupled to the ultrasound imaging system and configured to determine strains between two locations within the tissue from measured displacements and to estimate a difference in relaxation-times between the two locations from a difference in phases of the strains at the two locations.

* * * * *